US009284580B2

(12) United States Patent
Yang et al.

(10) Patent No.: US 9,284,580 B2
(45) Date of Patent: Mar. 15, 2016

(54) METABOLIC ENGINEERING OF CLOSTRIDIUM TYROBUTYRICUM FOR BUTANOL PRODUCTION

(76) Inventors: Shang-Tian Yang, Dublin, OH (US); Mingrui Yu, Columbus, OH (US)

(*) Notice: Subject to any disclaimer, the term of this patent is extended or adjusted under 35 U.S.C. 154(b) by 280 days.

(21) Appl. No.: 13/877,332

(22) PCT Filed: Sep. 30, 2011

(86) PCT No.: PCT/US2011/054376
§ 371 (c)(1), (2), (4) Date: Jul. 23, 2013

(87) PCT Pub. No.: WO2012/045022
PCT Pub. Date: Apr. 5, 2012

(65) Prior Publication Data

US 2013/0323809 A1 Dec. 5, 2013

Related U.S. Application Data

(60) Provisional application No. 61/389,060, filed on Oct. 1, 2010.

(51) Int. Cl.

| | |
|---|---|
| ***A61K 38/00*** | (2006.01) |
| ***C12P 7/16*** | (2006.01) |
| ***C12N 9/04*** | (2006.01) |
| ***C12N 9/02*** | (2006.01) |
| ***C12N 15/74*** | (2006.01) |

(52) U.S. Cl.
CPC ................. *C12P 7/16* (2013.01); *C12N 9/0006* (2013.01); *C12N 9/0008* (2013.01); *C12N 15/74* (2013.01); *Y02E 50/10* (2013.01)

(58) Field of Classification Search
CPC .... C12N 9/0006; C12N 9/0008; C12N 15/74; C12P 7/16
USPC ............................ 435/160, 252.3, 320.1, 471
See application file for complete search history.

(56) References Cited

U.S. PATENT DOCUMENTS

| | | | |
|---|---|---|---|
| 2008/0248540 | A1 | 10/2008 | Yang |
| 2009/0111154 | A1 | 4/2009 | Liao et al. |
| 2009/0269823 | A1 | 10/2009 | Bramucci et al. |
| 2010/0151544 | A1 | 6/2010 | Papoutsakis et al. |

FOREIGN PATENT DOCUMENTS

| | | | |
|---|---|---|---|
| WO | 2009082148 | A2 | 7/2009 |

OTHER PUBLICATIONS

Youngleson et al. Gene, (May 30, 1989) vol. 78, No. 2, pp. 355-64. Abstract.*
Fontaine et al. [Journal of Bacteriology, Feb. 2002, vol. 184, No. 3, p. 821-830].*
Ryan Sillers, et al., Aldehyde-Alcohol Dehydrogenase and/or Thiolase Overexpression Coupled With CoA Transferase Downregulation Lead to Higher Alcohol Titers and Selectivity in Clostridium acetobutylicum Fermentations, Biotechnology and Bioengineering, Jan. 1, 2009, pp. 38-49, vol. 102, No. 1.

* cited by examiner

*Primary Examiner* — Tekchand Saidha
(74) *Attorney, Agent, or Firm* — Standley Law Group LLP

(57) ABSTRACT

This invention relates to compositions, systems, and methods for producing biofuels, such as butanol, and related compounds. More specifically, provided are methods of making recombinant microorganizms having non-naturally occurring metabolic pathways for the production of biofuels, and methods of producing biofuels using such organizms. Also provided are metabolically engineered microorganizms capable of producing butanol from a substrate.

26 Claims, 10 Drawing Sheets

METABOLIC ENGINEERING OF CLOSTRIDIUM TYROBUTYRICUM FOR BUTANOL PRODUCTION

CROSS-REFERENCE TO RELATED APPLICATIONS

This application claims the benefit of priority from U.S. Provisional Patent Application No. 61/389,060, filed Oct. 1, 2010, which is hereby incorporated by reference in its entirety.

STATEMENT REGARDING FEDERALLY-SPONSORED R & D

This invention was made with government support under Award No. IIP-0810568, IIP-1026648 awarded by the National Science Foundation. The government has certain rights in the invention.

TECHNICAL FIELD

Metabolically engineered microorganisms and methods of producing biofuels, particularly metabolically engineered microorganisms and methods of producing biobutanol from sugars.

BACKGROUND OF THE INVENTION

With concerns about greenhouse gas emissions and uncertainty about the supply of oil, renewable biofuels have gained increasing attention. Bioethanol, the current major biofuel, is not an ideal replacement of gasoline because of its low energy density, high water solubility and high vapor pressure. Compared to ethanol, butanol is more hydrophobic, has a more similar energy content (27 MJ/L) to that of gasoline (32 MJ/L) and can be transported in the existing pipeline infrastructure. Thus, butanol is considered as a better drop-in biofuel than ethanol.

Butanol can be produced by anaerobic microorganisms such as *Clostridium acetobutylicum* and *Clostridium beijerinckii* in acetone-butanol-ethanol fermentation (ABE fermentation), which was once the second largest industrial fermentation in the world. In a typical ABE fermentation, butyrate and acetate are produced first, and then the culture undergoes a metabolic shift and solvents (butanol, acetone, and ethanol) are formed. Due to the complicated metabolic pathways involving acidogenesis and solventogenesis, plus spore-forming life cycle, ABE fermentation is difficult to control or manipulate. Furthermore, ABE fermentation usually suffers from low butanol yield (~20% w/w), titer (<15 g/L) and productivity (<0.5 g/L·h) because of butanol toxicity and production of other byproducts including acetone, ethanol, acetate and butyrate. The low reactor productivity, butanol yield, and final butanol concentration make biobutanol from ABE fermentation uneconomical for the fuel market.

Since the first oil crisis in the early 1980's, there have been numerous attempts to improve butanol production via metabolic engineering of *C. acetobutylicum* and process engineering to alleviate inhibition caused by butanol and facilitate product recovery. Genetic engineering of *C. acetobutylicum* has failed to result in large increases in butanol yields and product titers to economically favorable levels. This is largely due to the fact that high concentrations of butanol are toxic to the bacteria that produce the solvent. To date, no genetically engineered *C. acetobutylicum* and related strains can meet the requirements for industrial use in butanol production.

There have been efforts to engineer non-solventogenic microbes, including *E. coli, S. cerevisiae, B. subtilis, P. putida* and *L. brevis*, for butanol production because of their potentially higher butanol tolerance and because they are easier to clone than Clostridia. Some microbes, including several strains of *P. putida* can tolerate up to 6% (w/v) butanol, although the butanol toxic threshold is between 1% and 2% (w/v) for most microorganisms. Most *S. cerevisiae* strains are tolerant to 1% (v/v) butanol with 60% relative specific growth rate, and three strains can grow in 2% (v/v) butanol with 10%-20% relative growth rate. For *E. coli*, its growth rate decreased to 20%-40% and 40%-60% at 1% (v/v) butanol at 37° C. and 30° C., respectively, and no growth was observed at 2% (v/v) butanol.

The Clostridia's solventogenic pathway, which involves multiple genes, has been cloned and expressed in several microorganisms. However, the highest butanol titer obtained so far was only 0.580 g/L in *E. coli,* 0.300 g/L in *L. brevis,* 0.120 g/L in *P. putida,* 0.024 g/L in *B. subtilis*, and 0.0025 g/L in *S. cerevisiae*. The slow and reversible turn-over rate of *Clostridium* butyryl dehydrogenase complex (bdh) could limit the butanol production. A keto-acid pathway has also been expressed in *E. coli* for n-butanol production, achieving butanol titer of 800 mg/L. Recently, a higher n-butanol titer of 4.65 g/L was obtained using a chimeric pathway assembled from three different organisms (*R. eutrophus* pha, *C. acetobutylicum* hbd, crt, and *T. denticola* ter replacing bdh) and overexpressing native pyruvate dehydrogenase complex (aceEF.Ipd) in *E. coli*. Furthermore, by increasing the availability of NADH, which is required for butanol biosynthesis, approximately 15 g/L of n-butanol was produced from glucose by the recombinant *E. coli* with an approximately 80% theoretical yield. Nevertheless, it has remained desirable to find non-solventogenic hosts that can produce n-butanol at a titer comparable to or higher than that from solventogenic Clostridia, which usually produce 12 g/L to 16 g/L butanol in ABE fermentation.

SUMMARY OF THE INVENTIVE CONCEPT

Provided herein are metabolically-engineered microorganisms that include recombinant biochemical pathways useful for producing n-butanol from renewable biomass. Also provided herein are methods of producing biofuels using the microorganisms described herein.

The invention features recombinant microorganisms capable of producing butanol that are constructed by transferring into a host organism which naturally produces butyric acid as a main metabolic product a foreign gene that encodes an enzyme having both alcohol/aldehyde dehydrogenase and butanol dehydrogenase activity so that the recombinant microorganism is capable of converting butyryl-CoA to butanol. Alternatively, the microorganism may be engineered to overexpress aldehyde/alcohol dehydrogenase 2 (adhE2), and convert butyryl-CoA to butanol under the control of a native thiolase (thl) promoter.

In certain embodiments the host organism is *Clostridium tyrobutyricum*, and the gene that encodes an enzyme having both alcohol/aldehyde dehydrogenase and butanol dehydrogenase activity comes from *C. acetobutylicum.*

In certain embodiments the recombinant microorganism is capable of producing butanol from glucose. In other embodiments the recombinant microorganism is capable of producing butanol from other monosachharides, oligosaccharides, and polysaccharides.

In certain embodiments the recombinant microorganism is constructed by transferring to the host organism a foreign gene for inactivating acetate kinase or for inactivating phosphotransacetylase or for inactivating phosphotransbutyrylase. Optionally, these foreign genes may be ack, pta, or ptb knockouts, respectively.

In certain embodiments the recombinant microorganisms may be Ct(pCAAD), Ct(pSAD42), Ct(pMAD72), Ct(pMAD22), AckKO(pMAD72), AckKO(pMAD22), PtaKO(pMAD72), PtaKO(pMAD22), PtbKO(pMAD72), or PtbKO(pMAD22).

In another aspect, the invention features vectors that enable a host organism to produce increased amounts of butanol. The vectors may be plasmids that contain genes for carrying out the functions of alcohol/aldehyde dehydrogenase and butanol dehydrogenase. In certain embodiments the vectors contain the adhE2 gene. Depending on the embodiment, the vector may be pSAD42, pMAD72, or pMAD22. The vectors may be transferred into *C. tyrobutyricum* to overexpress adhE2 for butanol production from glucose or other monosaccharides, oligosaccharides, or polysaccharides, along with pta, ptb, or ack knockout genes for enhancing butanol production.

In another aspect, the invention features methods of producing butanol and other biofuels. In certain of these embodiments, the methods include culturing one or more different recombinant microorganisms in a culture medium, and accumulating butanol in the culture medium. In certain embodiments the methods include culturing recombinant microorganisms containing genes for overexpressing adhE2. In other embodiments the methods include culturing recombinant microorganisms that also contain genes for inactivating acetate kinase, genes for inactivating phosphotransacetylase, or genes for inactivating phosphotransbutyrylase. In certain embodiments of the methods the host organism is *C. tyrobutyricum*. In certain embodiments of the methods the culture medium includes glucose. In other embodiments of the methods the culture medium includes other carbon sources, such as starch, sucrose, fructose, galactose, mannitol, and xylose.

In another aspect, the invention features methods of metabolically engineering microorganisms capable of producing butanol from a substrate. The methods include obtaining microbial hosts capable of naturally producing butyric acid, and transferring to the microbial host a foreign gene that encodes an enzyme having alcohol/aldehyde dehydrogenase and butanol hydrogenase activity. In certain embodiments the methods also include transferring to the microbial host a foreign gene for inactivating acetate kinase, phosphotransbutyrylase, or phosphotransacetylase. In certain embodiments the microbial host is *C. tyrobutyricum.*

DETAILED DESCRIPTION

Figure 1:
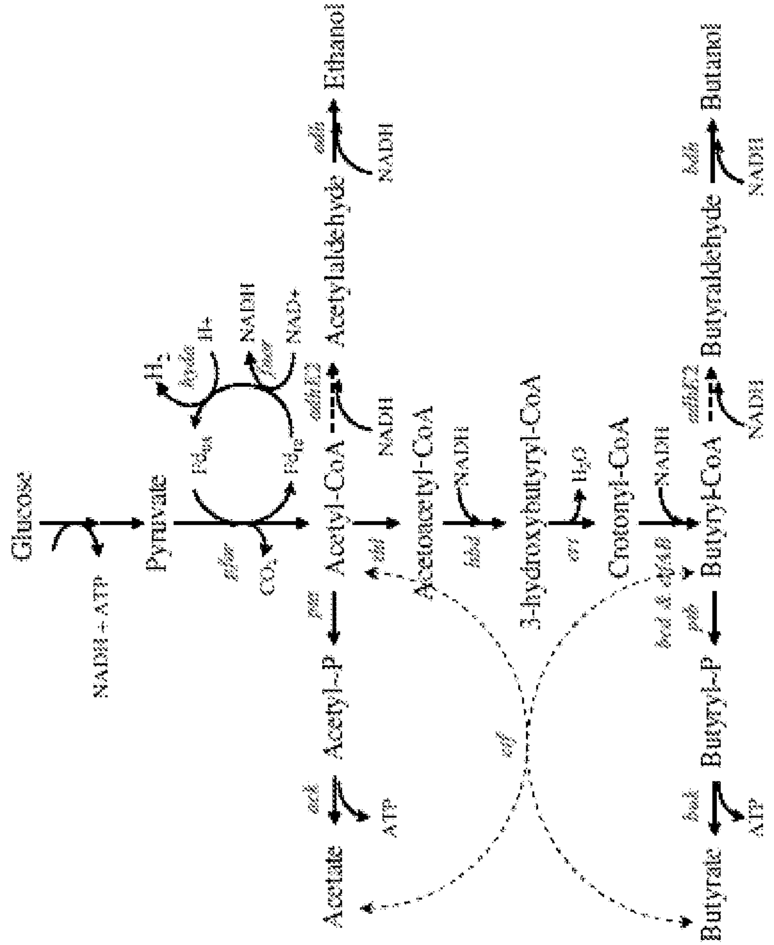
FIG. 1 depicts an exemplary metabolic pathway for *Clostridium tyrobutyricum*, where the pathways for butanol and ethanol formation shown in dotted lines are absent in wild-type *C. tyrobutyricum* and are introduced by overexpressing the adhE2 gene.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

Any publications discussed above and throughout the text are provided solely for their disclosure prior to the filing date of the present application. Nothing herein is to be construed as an admission that the inventors are not entitled to antedate such disclosure by virtue of prior disclosure.

The section headings used herein are for organizational purposes only and are not to be construed as limiting the described subject matter in any way. In addition, the materials, methods, and examples are illustrative only and not intending to be limiting. The use of the singular includes the plural unless specifically stated otherwise. Also, the use of "comprise," "comprises," "comprising," "contain," "contains," "containing," "include," "includes," and "including" are not intended to be limiting. It is understood that both the foregoing general description and the following detailed description are exemplary and explanatory only and are not restrictive of the invention. The articles "a" and "an" are used herein to refer to one or to more than one (i.e., to at least one) of the grammatical object of the article.

All numbers expressing quantities of ingredients, reaction conditions, and so forth used in the specification and claims are understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

As utilized in accordance with the embodiments provided herein, the following terms, unless otherwise indicated, shall be understood to have the following meanings:

The term "plasmid" refers to a circular nucleic acid vector. Generally, plasmids contain an origin of replication that allows many copies of the plasmid to be produced in a bacterial (or sometimes eukaryotic) cell without integration of the plasmid into the host cell DNA.

The term "construct" as used herein refers to a recombinant nucleotide sequence, generally a recombinant nucleic acid molecule, that has been generated for the purpose of the expression of a specific nucleotide sequence(s), or is to be used in the construction of other recombinant nucleotide sequences. In general, "construct" is used herein to refer to a recombinant nucleic acid molecule.

The term "host cell" refers to a cell that is to be transformed using the methods and compositions of the invention. In general, host cell as used herein means a microorganism cell into which a nucleic acid of interest is to be transformed.

The term “transformation” refers to a permanent or transient genetic change, preferably a permanent genetic change, induced in a cell following incorporation of non-host nucleic acid sequences. Transformation (or transduction, or transfection), can be achieved by any one of a number of means including electroporation, conjugation, microinjection, biolistics (or particle bombardment-mediated delivery), or *agrobacterium* mediated transformation.

The term “vector” generally refers to a polynucleotide that can be propagated and/or transferred between organisms, cells, or cellular components. Vectors include viruses, bacteriophage, pro-viruses, plasmids, phagemids, transposons, and artificial chromosomes, that are able to replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium.*

The term “promoter” refers to a minimal nucleic acid sequence sufficient to direct transcription of a nucleic acid sequence to which it is operably linked. The term “promoter” is also meant to encompass those promoter elements sufficient for promoter-dependent gene expression controllable for cell-type specific expression or inducible by external signals or agents; such elements may be located in the 5' or 3' regions of the naturally-occurring gene.

The term “native” or “wild-type” as used with a protein, enzyme, polynucleotide, gene, or cell, means a protein, enzyme, polynucleotide, gene, or cell that occurs in nature.

The term “n-butanol” generally refers to a straight chain isomer with the alcohol functional group at the terminal carbon. Recombinant microorganisms provided herein can express a plurality of target enzymes involved in pathways for the production of n-butanol from a suitable carbon substrate.

Accordingly, metabolically “engineered” or “modified” organisms are produced via the introduction of genetic material into a host or parental microorganism of choice thereby modifying or altering the cellular physiology and biochemistry of the microorganism. Through the introduction of genetic material the parental microorganism acquires new properties, e.g., the ability to produce a new, or greater quantities of, an intracellular metabolite. In an illustrative embodiment, the introduction of genetic material into a parental microorganism acquires new properties, e.g., the ability to produce a new, or greater quantities of, an intracellular metabolite. In an illustrative embodiment, the introduction of genetic material into a parental microorganism results in a new or modified ability to produce n-butanol. The genetic material introduced into the parental microorganism contains gene(s), or parts of genes, coding for one or more of the enzymes involved in a biosynthetic pathway for the production of n-butanol and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion, or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

Microorganisms provided herein are modified to produce metabolites in quantities not available in the parental organism. A “metabolite” refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism.

The disclosure provides recombinant microorganisms that produce n-butanol and include the expression or elevated expression of target enzymes such as aldehyde/alcohol dehydrogenase (adhE2) as compared to a parental microorganism. In addition, the modified microorganism may include a disruption, deletion or knockout of expression of phosphotransbutyrylase (ptb), phosphotransacetylase (pta), or acetate kinase (ack), as compared to a parental microorganism.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

As shown in FIG. 1, the pathways for butanol and ethanol formation (shown by the dotted lines) are absent in wild-type *C. tyrobutyricum* and are introduced by overexpressing the adhE2 gene. Key enzymes and genes in the pathway include the following: hydrogenase (hydra); pyruvate: ferredoxin oxidoreductase (pfor); ferredoxin $NAD^+$ oxidoreductase (fnor); acetate kinase (ack); phosphotransacetylase (pta); thiolase (MI); beta-hydroxybutyryl-CoA dehydrogenase (hbd); crotonase (crt); butyryl-CoA dehydrogenase (bcd); electron transferring flavoprotein (ett); phosphotransbutyrylase (ptb); butyrate kinase (buk); CoA transferase (ctt); alcohol dehydrogenase (adh); butanol dehydrogenase (bdh); aldehyde-alcohol dehydrogenase (adhE2).

Bacterial Strains and Growth Conditions

Bacterial strains and plasmids used in the examples are listed in Table 1.

TABLE 1

Bacterial strains and plasmids used in this study

| Strains or plasmids | Description | Reference or source |
|---|---|---|
| Strains | | |
| *C. tyrobutyricum* | ATCC 25755 | ATCC |
| AckKO | Ack knockout | Liu et al, 2006 |

TABLE 1-continued

| Bacterial strains and plasmids used in this study | | |
|---|---|---|
| Strains or plasmids | Description | Reference or source |
| PtbKO | Ptb knockout | Zhang, 2009 |
| PtaKO | Pta knockout | Zhu et al, 2005 |
| Ct(pCAAD) | ATCC 25755 with pCAAD | The examples |
| Ct(pSAD42) | ATCC 25755 with pSAD42 | The examples |
| Ct(pMTL007) | ATCC 25755 with pMTL007 | The examples |
| Ct(pMAD72) | ATCC 25755 with pMAD72 | The examples |
| Ct(pMAD22) | ATCC 25755 with pMAD22 | The examples |
| AckKO(pMAD72) | AckKO with PMAD72 | The examples |
| AckKO(pMAD22) | AckKO with pMAD22 | The examples |
| PtbKO(pMAD72) | PtbKO with pMAD72 | The examples |
| PtbKO(pMAD22) | PtbKO with pMAD22 | The examples |
| PtaKO(pMAD72) | PtaKO with pMAD72 | The examples |
| PtaKO(pMAD22) | PtaKO with pMAD22 | The examples |
| *E. coli* CA434 | *E. coli* HB101 with plasmid R702 | Williams et al, 1990 |
| Plasmids | | |
| pCAAD | ColE1 ori; $Amp^R$; $Em^R$; pIM13 ori; Paad::aad | Nair et al, 1994 |
| pSAD42 | ColE1 ori; $Amp^R$; $Em^R$; pIM13 ori; Paad::aad | The examples |
| pMTL82151 | ColE1 ori; $Cm^R$; pBP1 ori; TraJ; oriT | Heap et al, 2009 |
| pMTL007 | ColE1 ori; $Cm^R$; pCB102 ori; TraJ; oriT | Heap et al, 2007 |

TABLE 1-continued

| Bacterial strains and plasmids used in this study | | |
|---|---|---|
| Strains or plasmids | Description | Reference or source |
| pMAD72 | From pMTL007; Pthl::adhE2 | The examples |
| pMAD22 | From pMTL82151; Pthl::adhE2 | The examples |

Ack, acetate kinase; Ptb, phosphotransbutyrylase; Pta, phosphotransacetylase; KO, knock-out; ack, acetate kinase; adhE2, aldehyde-alcohol dehydrogenase; ori, origin; $Amp^R$, ampicillin resistance; $Em^R$, erythromycin resistance; $Cm^R$, chloramphenicol resistance; TraJ and oriT: genes for conjugation; ColE1, *E. coli* replicon; Paad, aad promoter from *C. acetobutylicum*; P thl: thl promoter from *C. tyrobutyricum*; pIM13, replicon from *B. subtilis;* pCB102, replicon from *C. butyricum*; pBP1, replicon from *C. botulinum.*

Bacterial Strains and Culture Media

*Clostridium tyrobutyricum* ("*C. tyrobutyricum*"), ATCC 25755 was the parental strain of various mutant strains (see Table 1) developed in this work. *C. acetobutylicum* ATCC 824 was used to extract adhE2 gene from its genome. *E. coli* DH5α (Invitrogen, Carlsbad, Calif.) was used in the preparation of recombinant plasmids and *E. coli* CA434 as the donor strain in conjugation described later. Unless otherwise noted, *C. tyrobutyricum* and *C. acetobutylicum* were grown anaerobically at 37° C. in Reinforced Clostridial Medium (RCM; Difco, Detroit, Mich.). Colonies were maintained on RCM (15 g/L agar) plates in the anaerobic chamber. These media were supplemented with 40 μg/mL erythromycin or 30 μg/mL thiamphenicol for transformant selection. *E. coli* was grown aerobically at 37° C. and 250 rpm in Luria-Bertani (LB) media supplemented with chloramphenicol (30 μg/mL), ampicillin (100 μg/mL) or kanamycin (50 μg/mL).

Plasmid Construction

Several recombinant plasmids were constructed and used to create various butanol-producing *C. tyrobutyricum* mutant strains (See Table 1). Table 2 below provides a list of exemplary oligonucleotide primers, as well as their nucleic acid sequence. It is understood that alternative sequences may also be used to amplify a target nucleic acid. Accordingly, the methods described herein are not limited solely to the primers described below.

TABLE 2

| Primers used in PCR amplification of adhE2 gene and thl promoter sequence. | |
|---|---|
| Primer | DNA Sequence |
| Amplification of adhE2 gene from ATCC 824 genomic DNA - Forward Primer (SEQ ID No: 1) | 5'-AT**GGATCC**TTTTATAAAGGAGTGTATATAAATGAAAG-3' |
| Amplification of adhE2 gene from ATCC 824 genomic DNA - Reverse Primer (SEQ ID No: 2) | 5'-TT**GGCGCC**ATAATGAAGCAAAGACTATTTTACATTC-3' |
| Amplification of adhE2 gene from plasmid pSAD42 - Forward Primer (SEQ ID No: 3) | 5'-AT***GGATCC***ATAAATATTT**AGGAGG**AATAGTCATGAAAGTT ACAAATCAAAAAGAAC-3' |
| Amplification of adhE2 gene from plasmid pSAD42 - Reverse Primer (SEQ ID No: 4) | 5'-TCTA***CCGCGG***ATAATGAAGCAAAGACTATTTTACATTC-3' |
| Amplification of thl promoter sequence from ATCC 25755 genomic DNA - Forward Primer (SEQ ID No: 5) | 5'-AGCT**AAGCTT**CTGAATATTCAGCGAAAATAG-3' |
| Amplification of thl promoter sequence from ATCC 25755 genomic DNA - Reverse Primer (SEQ ID No: 6) | 5'-TCTA***CCGCGG***ACGTC***GGATCC***AAATTTAAATTGATTACAAA CCTTTTTACC-3' |

Figure 2:
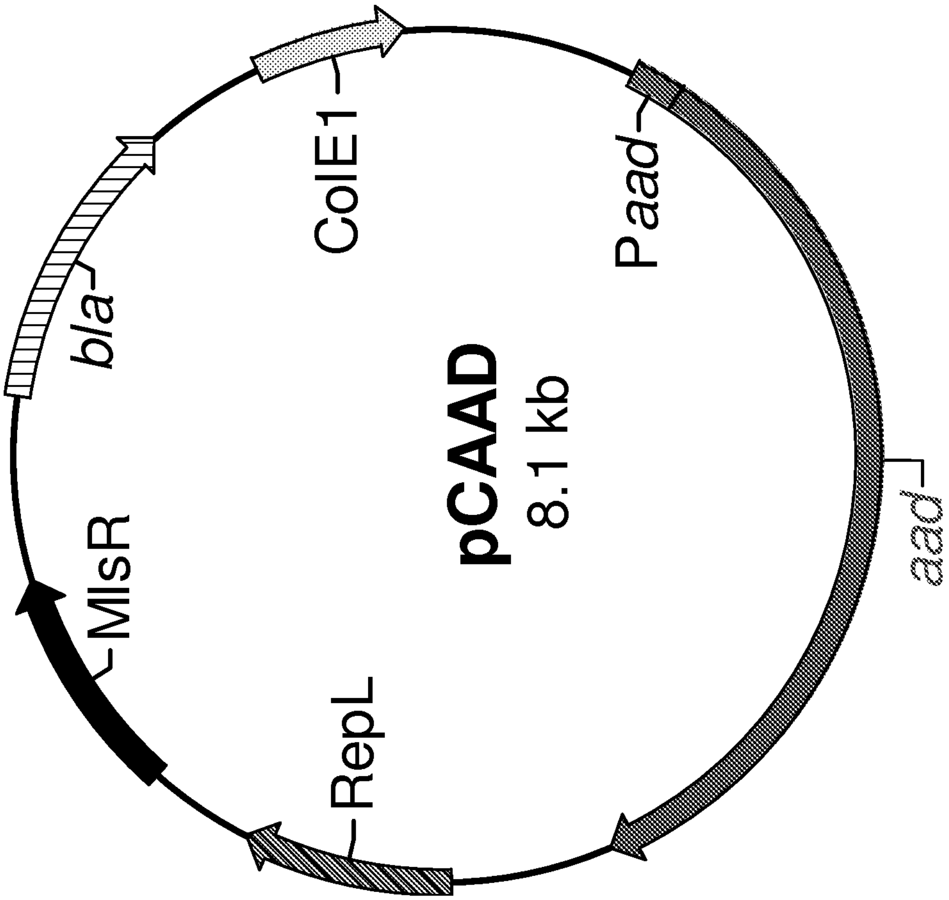
FIG. 2 depicts a map of plasmid pCAAD.
Figure 3:
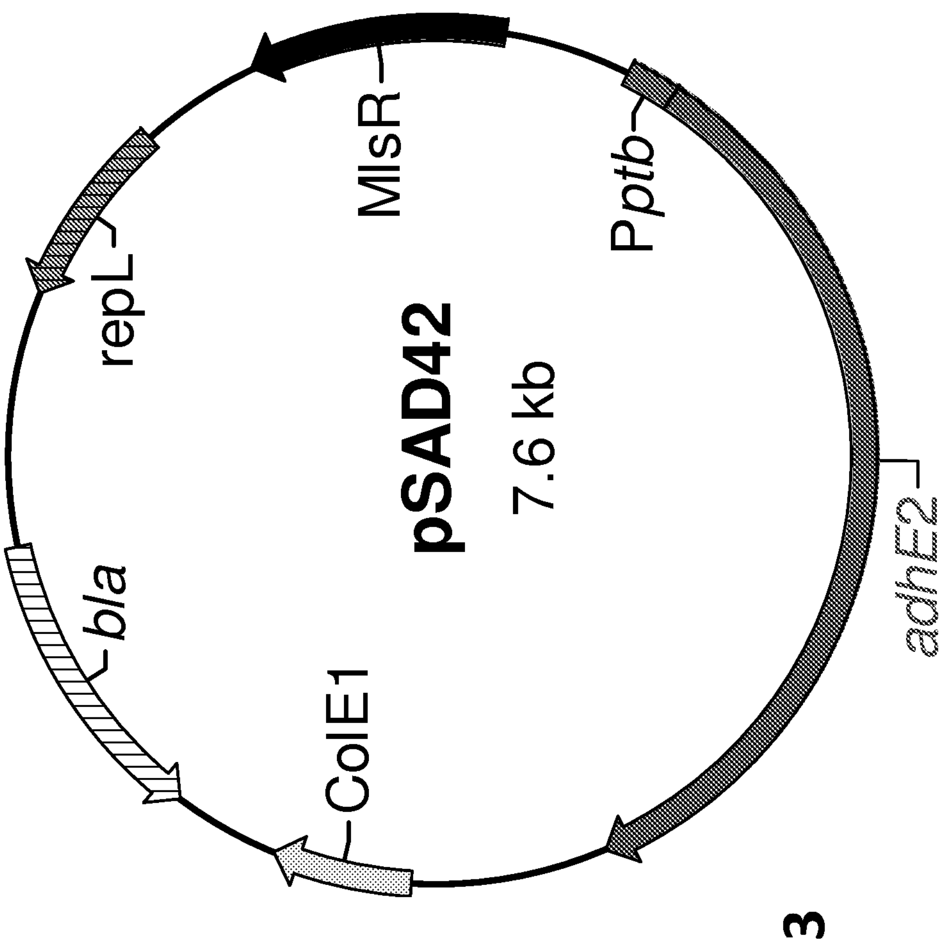
FIG. 3 depicts a map of plasmid pSAD42.
Figure 4:
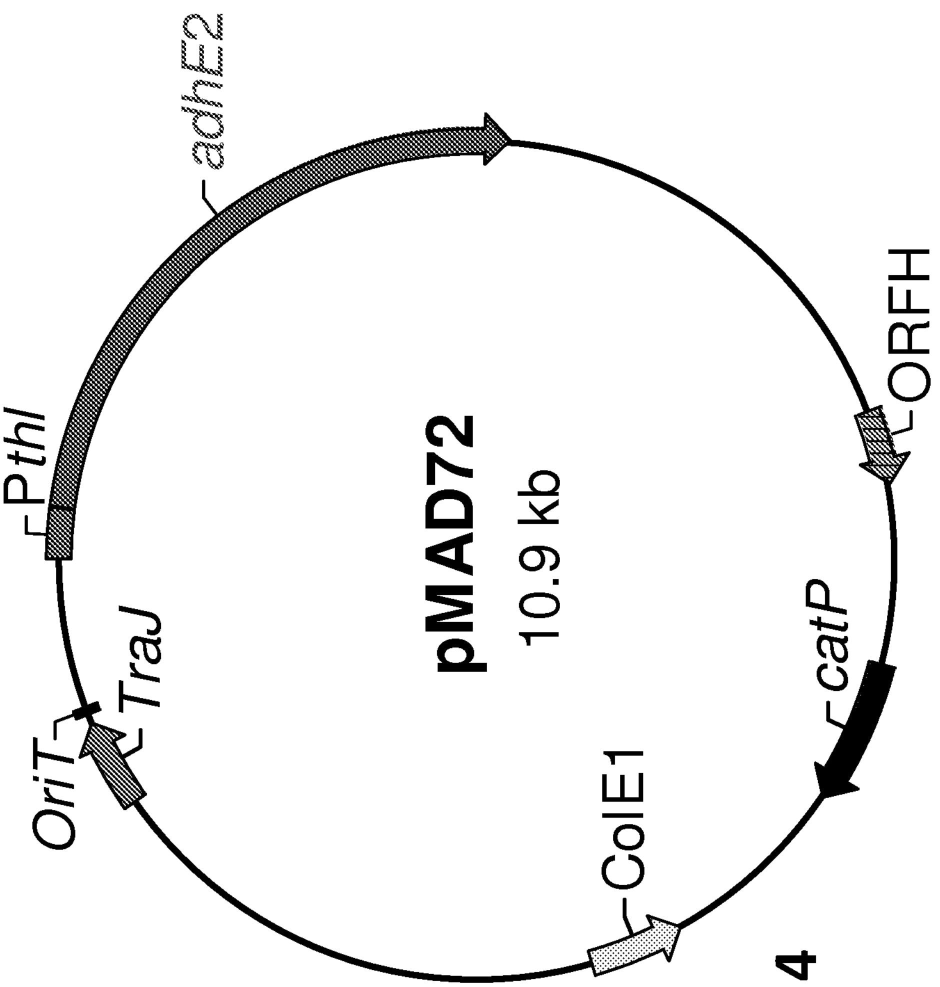
FIG. 4 depicts a map of plasmid pMAD72.

Plasmid pCAAD, a map of which is depicted in FIG. 2, containing aad gene and native aad promoter from *C. acetobutylicum* ATCC 824, was obtained from Professor G. N. Bennett of Rice University (Nair et al., 1994). Plasmids pSAD42 (map depicted in FIG. 3) and pMAD72 (map depicted in FIG. 4) were created by cloning adhE2 into plasmids pSOS94 (Genbank Accession No. AY187685, SEQ ID No: 7) and pMTL007 (Genbank Accession No. EF525477, SEQ. ID No: 8), respectively. The construction of these recombinant plasmids is briefly described below.

The adhE2 gene (Genbank Accession No. AF321779, SEQ. ID No: 9) was PCR-amplified from *C. acetobutylicum* ATCC 824 genomic DNA. The PCR product was purified and digested with BamHI (New England Biolabs, Ipswich, Mass.) and Sfol (New England Biolabs, Ipswich, Mass.), and then ligated into plasmid pSOS94 digested with the same restriction enzymes to generate recombinant pSAD42. To construct recombinant pMAD72, adhE2 was PCR-amplified from pSAD42, and thl promoter (Genbank Accession No. HM989902, SEQ. ID No: 10) was PCR-amplified from *C. tyrobutyricum* ATCC 25755 genomic DNA. The PCR product of thl promoter (Pthl) was ligated into pGEM-T vector (Promega, Madison, Wis.) to generate pGEM-T-Pthl. Plasmid pGEM-T-Pthl and adhE2 PCR product were digested with BamHI and SacII (New England Biolabs, Ipswich, Mass.) and ligated to generate pGEM-T-PthladhE2. PthladhE2, from pGEM-T-PthladhE2 after treating with HindIII (New England Biolabs, Ipswich, Mass.) and SacII, was ligated into plasmids pMTL007 and pMTL82151, after HindIII and SacII digestion, to generate pMAD72 and pMAD22, respectively. All recombinant plasmids were transformed into *E. coli* DH5α (Invitrogen) and purified plasmids were confirmed by DNA sequencing.

Transformation

Unless otherwise noted, all transformation procedures were performed in an anaerobic chamber. Plasmids of pCAAD and pSAD42 were transformed into *C. tyrobutyricum* by electroporation following the previously described method. Two mutants, Ct(pCAAD) and Ct(pSAD42), were obtained by transforming ATCC 25755 with pCAAD or pSAD42, respectively.

*C. tyrobutyricum* was also transformed with pMAD72 via conjugation following the procedures described below. The donor strain, *E. coli* CA434 (*E. coli* HB101 with IncPβ conjugative plasmid R702), was first transformed with the recombinant plasmid to be mobilized by electroporation, and then the transformed cells were collected by centrifugation after culturing in LB medium containing 30 μg/mL chloramphenicol at 37° C. and 250 rpm overnight to reach OD600 1.5~2.0. About 3 mL of the donor *E. coli* cells were then washed once in 1 mL of sterile phosphate-buffered saline (PBS) and resuspended into 0.4 mL of the recipient *C. tyrobutyricum* cells, which were grown overnight to OD600 2.0~3.0 in the RCM medium at 37° C. The cell mixture was then pipetted onto well-dried RCM agar plate and incubated at 37° C. for 24 hours for mating. One milliliter of the RCM medium was then applied to each conjugation plate to harvest cells, which were then re-plated on RCM plates with 25 μg/mL thiamphenicol (selection for plasmid uptake) and 200 μg/mL D-cycloserine (counter selection for *E. coli*). Plates were incubated for 48 to 96 hours or until colonies were apparent. Four mutants, Ct(pMAD72), AckKO(pMAD72), PtaKO(pMAD72) and PtbKO(pMAD72), were obtained by transforming pMAD72 into *C. tyrobutyricum* ATCC 25755, AckKO with ack knock-out (using a partial ack gene having GenBank Accession No. AY706093; SEQ. ID No. 11), PtaKO with pta knock-out (using a partial pta gene having GenBank Accession No. AY572855; SEQ. ID No. 12) and PtbKO with ptb knock-out (using a partial ptb fragment identical to the ptb sequence from *C. acetobutylicum*, ATCC 824, gene ID1119259, E.C. 2.1.3.19), respectively. Likewise, pMAD22 was also transformed into *C. tyrobutyricum* ATCC 25755, AckKO, PtaKO, and PtbKO to obtain Ct(pMAD22), AckKO(pMAD22), PtaKO(pMAD22), and PtbKO (pMAD22), respectively. In addition, *C. tyrobutyricum* ATCC 25755 was also transformed with pMTL007 (without adhE2 gene) to obtain the strain Ct(pMTL007), which was used as a control in the fermentation kinetics study described below. AckKO(pMAD72) was deposited with the ATCC in Manassas, Va. prior to the filing of this application, and was granted ATCC Deposit No. PTA-12145.

Fermentation Kinetics

Unless otherwise noted, batch fermentations with *C. tyrobutyricum* mutants were carried out in serum bottles containing P2 medium (50 g/L glucose, 3 g/L yeast extract, 1 g/L tryptone, 2 g/L $K_2HPO_4$, 2 g/L $KH_2PO_4$, 0.2 g/L $MgSO_4$, 0.01 g/L $MnSO_4$, 0.01 g/L $FeSO_4$, 0.01 g/L NaCl) supplemented with 40 μg/mL erythromycin or 25 μg/mL thiamphenicol as required. Each bottle containing 40 mL of the medium was inoculated with 0.4 mL of cells from an overnight culture in RCM. The fermentation was carried out at 37° C. and the medium pH was maintained between 5.0 and 6.5 by adding NaOH solution twice a day. Samples were taken at regular intervals to monitor cell growth, substrate (glucose) consumption and production of butanol, ethanol, acetic acid and butyric acid during the fermentation.

AdhE2 Enzyme Activity Assays

The activities of butyraldehyde dehydrogenase and butanol dehydrogenase of adhE2 were measured by monitoring NADH consumption at 365 nm according to the method described before with some modifications. Cells were collected from 100 mL fermentation broth by centrifugation at 10000 g for 10 min using tightly sealed centrifuge tubes purged by nitrogen gas. The cell pellet was washed with Tris-HCl buffer (0.1 M, pH 7.5) once and resuspended in 5 mL of the same Tris-HCl buffer. Lysis was carried out by using a French press with one passage at 77 MPa. Supernatant was collected by centrifugation at 15000 g for 10 minutes and used for enzyme activity assay. Enzyme activity was calculated on the basis of a molar NADH extinction coefficient of 3.4 $cm^{-1}$ $mM^{-1}$. One unit of enzyme activity was defined as the amount of enzyme which converts 1 μmol NADH per minute under the reaction conditions. Protein concentration in cell extract was determined using the Bio-Rad protein assay kit (Bio-Rad Laboratories, Richmond, Calif.) with bovine serum albumin as standard.

Butanol Tolerance

To evaluate the butanol tolerance of various *C. tyrobutyricum* mutants and *C. beijerinckii* ATCC 55025, cells were cultured in 50 mL centrifuge tubes, with caps tightly sealed, in an anaerobic chamber. Each tube containing 5 mL RCM medium and butanol at a concentration of up to 2% (v/v) was inoculated with 0.2 mL of cells from an overnight culture in RCM. Cell growth was monitored by measuring the optical density at 600 nm (OD600) of the culture broth. The specific growth rates at various initial butanol concentrations were estimated from OD600 data.

Analytical Methods

Cell density was analyzed by measuring the optical density of cell suspension at 600 nm using a spectrophotometer (UV-16-1, Shimadzu, Columbia, Md.). The glucose concentration was determined with a YSI 2700 Select Biochemistry Analyzer (Yellow Springs, Ohio). Butanol, ethanol, acetic acid and butyric acid were analyzed with a gas chromatograph (GC) (GC-2014 Shimadzu, Columbia, Md.) equipped with a flame ionization detector (FID) and a 30.0 m fused silica column (Stabilwax-DA, 0.25 mm film thickness and 0.25 mm ID, Restek, Bellefonte, Pa.). The GC was operated at an injection temperature of 200° C. with 1 μL of sample injected with an auto injector (AOC-20i, Shimadzu). The column temperature was initially held at 80° C. for 3 min, then increased at a constant rate of 30° C. per min to 150° C., and held at 150° C. for 3.7 min.

Butanol Production by Mutants

Figure 5:
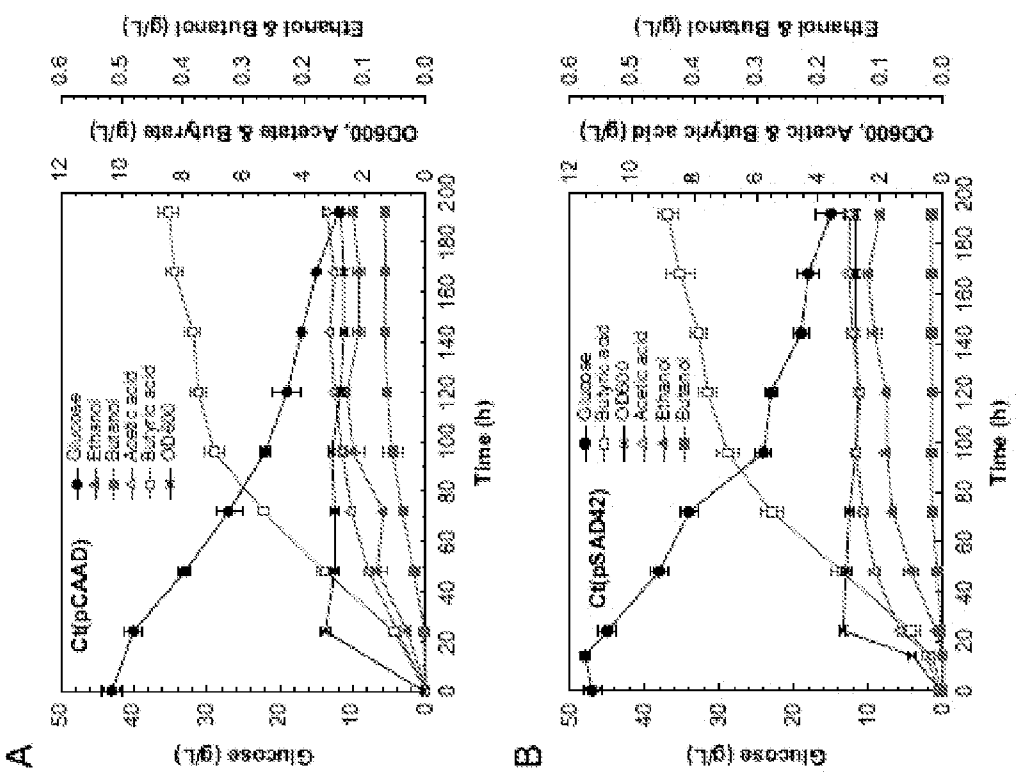
FIG. 5 depicts fermentation kinetics of *C. tyrobutyricum* mutants Ct(pCAAD) (Panel A) and Ct(pSAD42) (Panel B).

The wild-type strain (ATCC 25755) does not produce any detectable butanol from glucose because it does not have aldehyde/alcohol dehydrogenase genes needed to convert butyryl-CoA to butanol. Mutants were selected and tested for alcohol (ethanol and butanol) production in batch fermentations with glucose as the substrate following the procedure outlined under Fermentation Kinetics. FIG. 5 is a graphical representation of glucose consumption and product formation from batch fermentations with *C. tyrobutyricum* mutants Ct(pCAAD) and Ct(pSAD42). As shown in FIG. 5, both *C. tyrobutyricum* mutants Ct(pCAAD) and Ct(pSAD42) mainly produce butyric acid and acetic acid although butanol and ethanol are also produced. The final butanol titers obtained in these fermentations are 0.067 g/L in Ct(pCAAD) and 0.019 g/L in Ct(pSAD42). Furthermore, these mutants were not stable and could not be maintained in liquid cultures, suggesting poor plasmid stability in the host.

Figure 6:
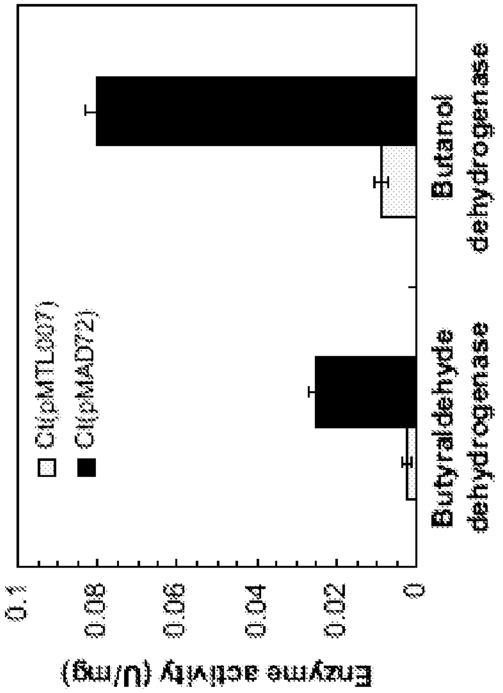
FIG. 6 depicts a comparison of butyraldehyde dehydrogenase and butanol dehydrogenase activities of *C. tyrobutyricum* mutant Ct(pMAD72) and Ct(pMTL007).
Figure 7:
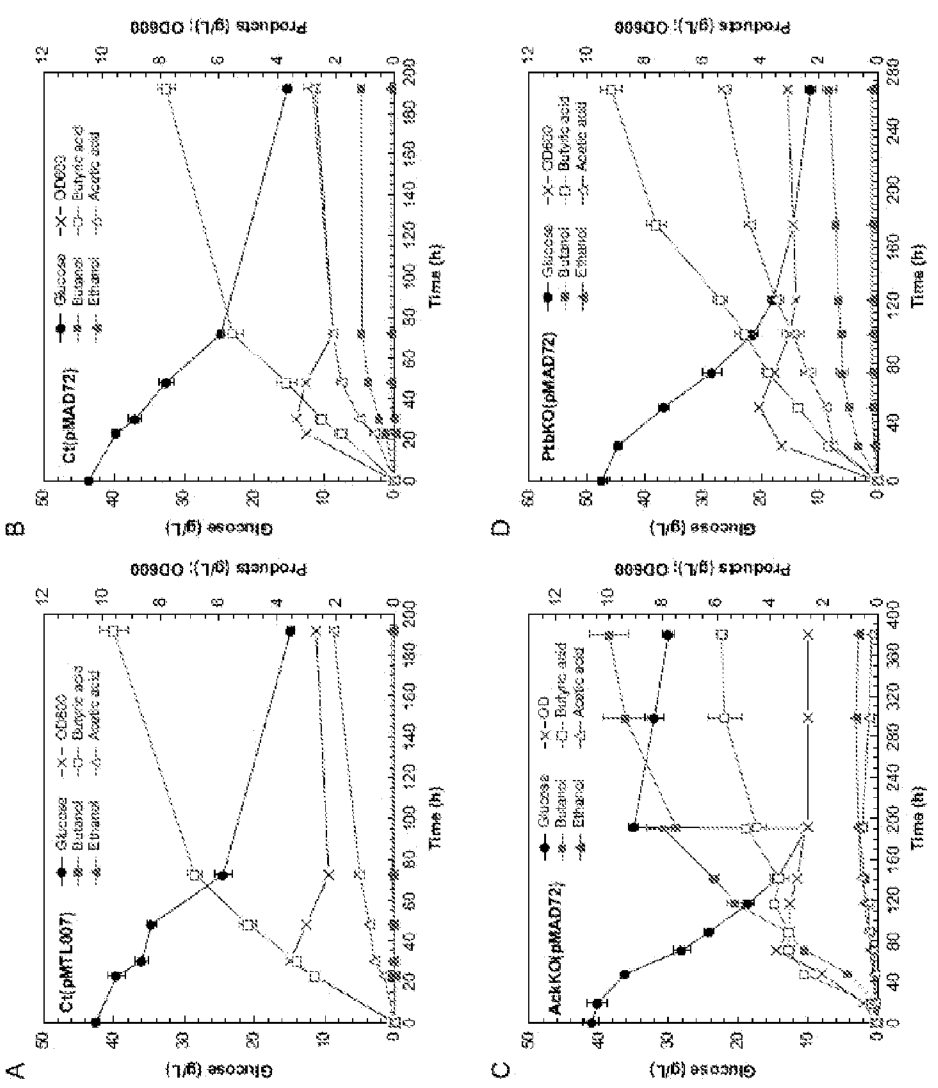
FIG. 7 depicts fermentation kinetics of *C. tyrobutyricum* mutants with plasmid pMAD72.

Plasmid pMTL007 with native thl promoter from *C. tyrobutyricum* was used to express adhE2 gene in *C. tyrobutyricum* for butanol production. The native thl promoter is a strong and constitutive promoter and was thus used to control the expression of adhE2 gene. As can be seen in FIG. 6, the activities of butyraldehyde dehydrogenase (0.025 U/mg) and butanol dehydrogenase (0.08 U/mg) of adhE2 increased about 10-fold in the mutant Ct(pMAD72) as compared to those in the wild-type control. Consequently, mutant Ct(pMAD72) produced 1.1 g/L butanol and 0.14 g/L ethanol in batch fermentation while the control (wild type with pMTL 007 without adhE2) produced little or no detectable amounts of butanol and ethanol (see FIG. 7). Compared to the control, the mutant Ct(pMAD72) produced less butyric acid (7.8 g/L vs. 9.7 g/L for the control) and more acetic acid (2.8 g/L vs. 2.1 g/L for the control). It is theorized that the decreased butyric acid production can be attributed to the conversion of some butyryl-CoA to butanol, whereas the slightly increased acetic acid production could be due to the need to compensate for the loss of ATP generation from butyric acid biosynthesis in the mutant. Compared to mutants with pCAAD and pSAD42, mutant Ct(pMAD72) with pMAD72 produced much more butanol (1.1 g/L vs.<0.1 g/L).

FIGS. 7C and 7D are graphical representations of glucose consumption and product formation from batch fermentations with ack and ptb knockout mutants of *C. tyrobutyricum* expressing adhE2. With ptb knockout, mutant PtbKO(pMAD72) produced 1.7 g/L butanol, a 55% increase over the 1.1 g/L produced by Ct(pMAD72). The increase in butanol production was expected as less butyryl-CoA was converted to butyric acid because of the ptb knockout. However, butyric acid production was still high (9.2 g/L vs. 9.7 g/L by Ct(pMTL007) and 7.8 g/L by Ct(pMAD72)). Compared to Ct(pMAD72), more acetic acid (5.3 g/L) and ethanol (0.2 g/L) were produced in PtbKO(pMAD72), indicating that more carbon substrates were directed towards C2 products.

A higher butyrate/acetate ratio with higher butyrate titer and yield were obtained with *C. tyrobutyricum* mutant with ack knockout. This mutant was used as the host to express adhE2 for butanol production, and the fermentation results are shown in FIG. 7C. Compared to Ct(pMAD72), AckKO(pMAD72) produced significantly more butanol (10.0 g/L vs. 1.1 g/L) and ethanol (0.7 g/L vs. 0.14 g/L) and less butyric acid (5.8 g/L vs. 7.8 g/L) and acetic acid (0.22 g/L vs. 2.8 g/L). The reduced acetic acid production in AckKO(pMAD72) can be attributed to the blocking of acetate biosynthesis pathway by ack knockout, which also resulted in increased butanol production because of increased carbon flux toward butyryl-CoA. As expected, AckKO(pMAD72) produced more C4 products (15.8 g/L butanol and butyric acid) and fewer C2 products (0.29 g/L acetic acid and ethanol) than did Ct(pMAD72) (8.9 g/L C4 products and 2.94 g/L C2 products) and PtbKO(pMAD72) (10.9 g/L C4 products and 5.5 g/L C2 products) because of the greater carbon flux toward butyryl-CoA than toward acetyl-CoA in AckKO(pMAD72). Also, AckKO(pMAD72) had a significantly lower specific growth rate than the other mutants studied (see Table 3 below) presumably because reduced acetate and butyrate production resulted in less ATP generation.

TABLE 3

Comparison of cell growth and final product concentrations from various mutant strains of *C. tyrobutyricum*.

| Strain | Max. OD600 | Specific growth rate ($h^{-1}$) | Butanol (g/L) | Butyrate (g/L) | Ethanol (g/L) | Acetate (g/L) | C4/C2 ratio (mol/mol) |
|---|---|---|---|---|---|---|---|
| Ct-WT | 3.4 ± 0.11 | 0.208 ± 0.003 | 0 | 9.26 ± 0.13 | 0.11 ± 0.02 | 2.1 ± 0.12 | 2.82 ± 0.19 |
| Ct(pCAAD) | 3.3 ± 0.15 | 0.189 ± 0.004 | 0.067 ± 0.004 | 8.45 ± 0.30 | 0.12 ± 0.006 | 3.2 ± 0.21 | 1.77 ± 0.12 |
| Ct(pSAD42) | 3.2 ± 0.10 | 0.199 ± 0.010 | 0.019 ± 0.002 | 8.85 ± 0.32 | 0.12 ± 0.006 | 3.0 ± 0.20 | 1.9 ± 0.13 |
| Ct(pMTL007) | 3.4 ± 0.09 | 0.206 ± 0.004 | 0 | 9.7 ± 0.47 | 0.08 ± 0.02 | 2.1 ± 0.26 | 3.0 ± 0.24 |
| Ct(pMAD72) | 3.5 ± 0.08 | 0.180 ± 0.002 | 1.1 ± 0.1 | 7.8 ± 0.29 | 0.14 ± 0.01 | 2.8 ± 0.30 | 2.1 ± 0.28 |
| PtbKO(pMAD72) | 4.0 ± 0.10 | 0.195 ± 0.005 | 1.7 ± 0.25 | 9.2 ± 0.36 | 0.2 ± 0.005 | 5.3 ± 0.22 | 1.4 ± 0.06 |
| AckKO(pMAD72) | 3.5 ± 0.20 | 0.115 ± 0.011 | 10.0 ± 0.71 | 5.8 ± 0.21 | 0.7 ± 0.035 | 0.22 ± 0.035 | 10.6 ± 0.55 |

Data are mean ± s.d. (n = 3).

Figure 8:
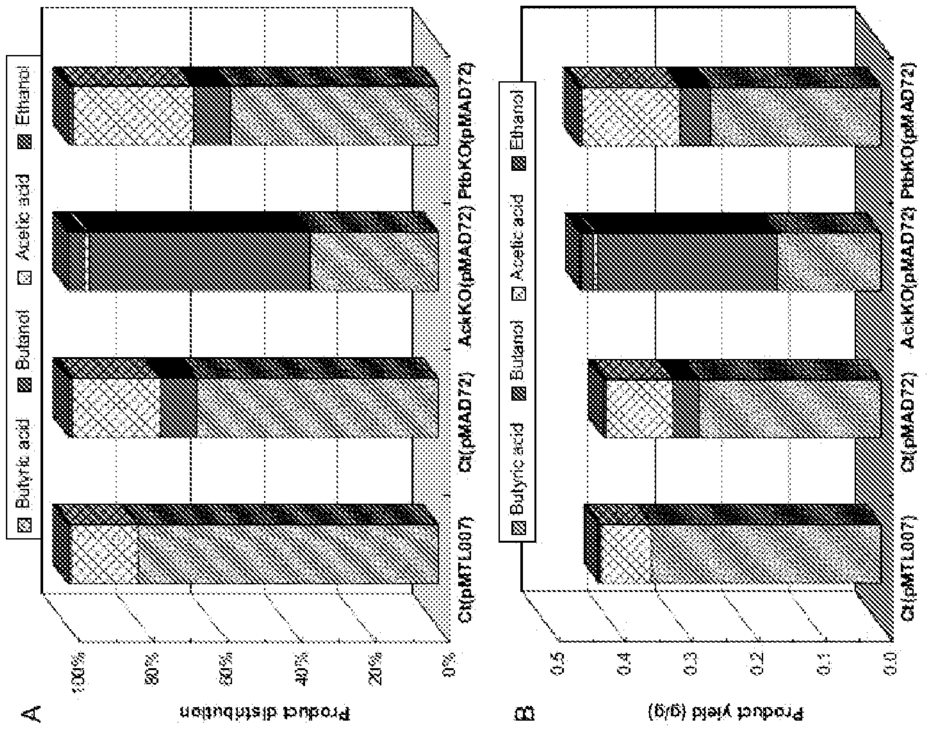
FIG. 8 depicts product distribution and yields from glucose in various *C. tyrobutyricum* mutants.

Table 3 summarizes the fermentation results from all mutants. With AckKO(pMAD72), one mol glucose yielded 0.64 mol butanol and 0.31 mol butyric acid, together accounting for 95% glucose fermented. The ratio of its C4 products (butanol and butyric acid) to C2 products is 10.6, much higher than 3.0 in wild-type. With PtbKO(pMAD72) one mol glucose produced 0.11 mol butanol and 0.50 mol butyric acid, and with Ct(pMAD72), one mol glucose produced 0.046 mol butanol and 0.42 mol butyric acid. FIG. 8 shows the product distribution and yields from glucose in various mutants (Panel A: product distribution, Panel B: product yields). The mutant AckKO(pMAD72) produced the highest amount of butanol (10.0 g/L) with 66% theoretical yield or 0.27 g/g glucose fermented.

Figure 9:
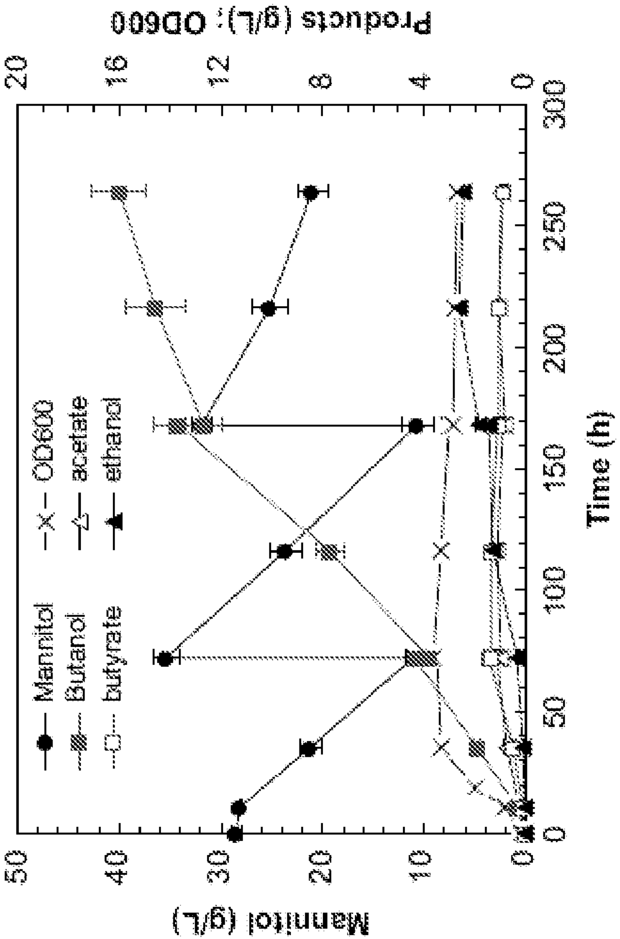
FIG. 9 depicts fermentation kinetics of AckKO(pMAD22) with mannitol as the substrate.

FIG. 9 shows the fermentation kinetics of AckKO(pMAD22) with mannitol as the substrate in serum bottles.

Higher butanol titer (~16 g/L vs. 10 g/L) and yield (~30.6% vs. 27% w/w) were obtained with lower acetate and butyrate production (~1.0 g/L vs.>5 g/L) when the more reduced substrate (mannitol vs. glucose) was used in the fermentation. When the fermentation was carried out in a bioreactor with pH controlled at ~6.0 in a rich medium with mannitol as the substrate, ~20.5 g/L of butanol was produced in ~60 hours with a butanol yield of ~33% (w/w) and productivity of 0.32 g/L/h.

Reducing hydrogen production by blocking or inhibiting hydrogenase can direct more reducing power to butanol production. Thus, using a hydrogenase inhibitor, such as methyl viologen or neutral red, significantly decreased acids production and enhanced butanol production from glucose, thus increasing the butanol yield and productivity. In batch fermentation in serum bottles, butanol production by AckKO (pMAD22) reached 10.6 g/L within 48 hours and butanol yield increased to 0.28 g/g glucose, whereas acetate and butyrate production decreased to less than 1 g/L. This work illustrated that inhibiting hydrogenase to reduce or block hydrogen production can greatly enhance butanol production and decrease acid production from glucose.

Besides glucose and mannitol as illustrated in the above examples, other common carbon sources, including starch, sucrose, fructose, galactose, and pentoses such as xylose, can also be readily converted to butanol by the various mutants of *C. tyrobutyricum* expressing the adhE2 gene.

Figure 10:
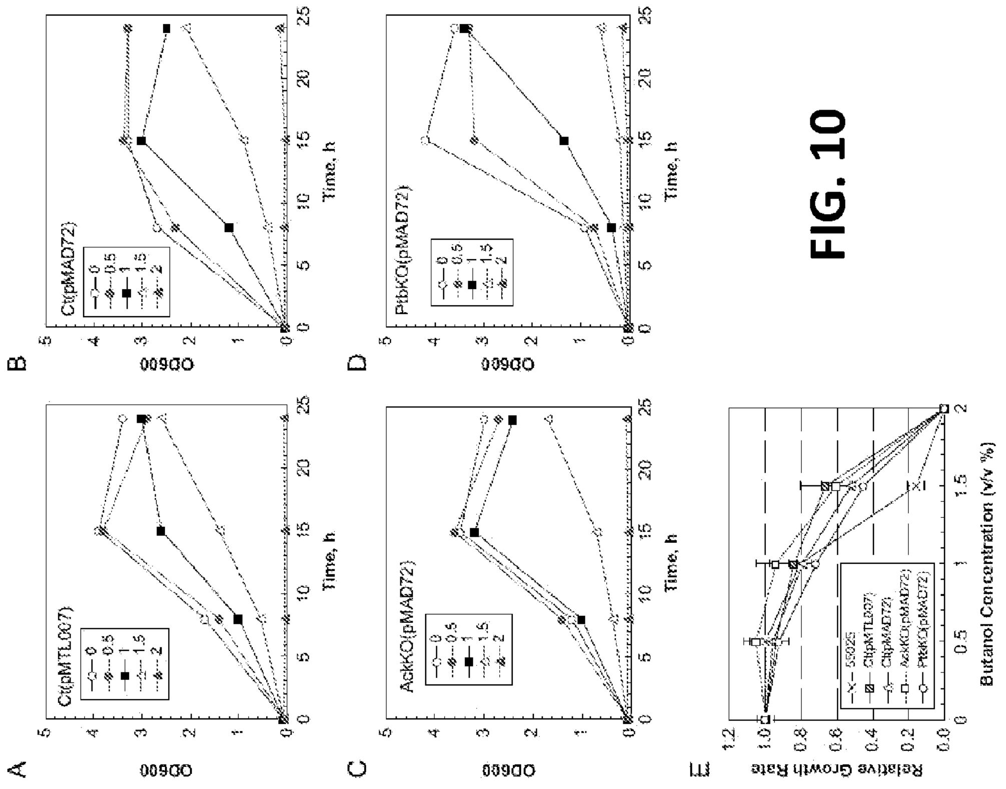
FIG. 10 depicts the effects of butanol on the growth of various *C. tyrobutyricum* mutants.

Butanol, with a four-carbon chain length, is more toxic to microbes than ethanol. Butanol tolerance is a critical factor limiting a cell's ability to produce butanol. To assess butanol tolerance, the effect of butanol concentration in the culture medium on cell growth was studied, and the results are shown in FIG. 10 (Panel A: Ct(pMTL007); Panel B: Ct(pMAD72); Panel C: AckKO(pMAD72); Panel D: PtbKO(pMAD72); Panel E: Relative Growth Rate. In general, 0.5% (v/v) butanol does not have any apparent effect on cell growth for the strains studied. As the butanol concentration increases, growth inhibition is observed. Cell growth decreases by from about 5% to more than 20% at 1.0% (v/v) butanol. At 1.5% (v/v) butanol, cell growth decreases by from about 30% to about 50%. At 2.0% (v/v) butanol, no significant cell growth was observed for the first 24 hours; however, all strains started to grow after 2 days. These results showed that *C. tyrobutyricum* can tolerate up to 1.5% (v/v) butanol without adaptation and up to about 2.0% (v/v) butanol after adaptation. *C. beijerinckii* ATCC 55025 growth rate was reduced ~20% and ~85% at 1% and 1.5% (v/v) butanol, respectively (FIG. 10E), and was completely inhibited by 2% (v/v) butanol as no cell growth was observed even after 10 days incubation. Most solventogenic Clostridia cannot grow at butanol concentrations higher than 1% (v/v) to 1.5% (v/v). Therefore, *C. tyrobutyricum* with high butanol tolerance is a favorable host for butanol production.

It will be recognized that *Clostridium* strains may be engineered that can not only produce butanol from glucose directly, but also from different polysaccharides and oligosaccharides that may be reduced down to their basic glucose units, and other monosaccharides such as xylose, galactose, and fructose. Lignocellulosic biomass, which is often lower in cost than sugars such as glucose or sucrose, may be used as a substrate for butanol production. Although *C. tyrobutyricum* is used to exemplify the present invention, other butyric acid producing bacteria including *C. butyricum, C. cellulovorans*, and *C. thermobutyricum* can also be used as the host and engineered to produce butanol using the same metabolic engineering technique disclosed in this invention.

Most butyric acid-producing Clostridia ferment glucose, xylose, lactose, starch and glycerol for cell growth and butyric acid production. Other substrates such as cellulose and $CO_2$ can also be used by some butyrate-producing Clostridia. For example, *C. carboxidivorans* and *Butyribacterium methylotrophicum* can utilize carbon monoxide and carbon dioxide and hydrogen to produce butyric acid. *C. cellulovorans, C. carboxidivorans, C. polysaccharolyticum* and *C. populeti* can use cellulose for butyrate synthesis. *C. kluyveri* can produce butyric acid as a major product from ethanol and acetate as substrates. These bacteria thus can also be used as hosts and engineered to produce butanol from different carbon sources. The preferred strains for commercial uses are those with high butanol tolerance, yield and productivity.

OTHER EMBODIMENTS

The foregoing description and Examples detail certain specific embodiments of the invention and describe the best mode contemplated by the inventors. It will be appreciated, however, that no matter how detailed the foregoing may appear, the invention can be practiced in many ways and the invention should be construed in accordance with the appended claims and any equivalents thereof.

What is claimed is:

1. A recombinant microorganism capable of producing butanol, which is constructed by transferring a heterologous DNA comprising the base sequences of SEQ ID No: 9 and SEQ ID No: 10 into a non-solventogenic host organism.

2. The recombinant microorganism of claim 1, wherein the host organism is *Clostridium tyrobutyricum.*

3. The recombinant microorganism of claim 2, wherein the host organism has been transformed with vector pMAD72.

4. The recombinant microorganism of claim 2, wherein the host organism has been transformed with vector pMAD22.

5. The recombinant microorganism of claim 1, wherein the recombinant microorganism is capable of producing butanol from glucose.

6. The recombinant microorganism of claim 4, wherein the recombinant microorganism is capable of producing butanol at a titer greater than 10 g/L and a yield greater than 0.3 g/g substrate.

7. The recombinant microorganism of claim 1, wherein the recombinant microorganism is capable of producing butanol from a monosaccharide, oligosaccharide, or polysaccharide.

8. The recombinant microorganism of claim 1, which is further constructed by transferring a foreign gene for inactivating acetate kinase to the host organism.

9. The recombinant microorganism of claim 1, which is further constructed by transferring a foreign gene or a portion thereof for inactivating phosphotransbutyrylase to the host organism.

10. The recombinant microorganism of claim 1, which is further constructed by transferring a foreign gene for inactivating phosphotransacetylase to the host organism.

11. The recombinant microorganism of claim 1, wherein the transfer of SEQ ID NO: 9 is accomplished using a vector that includes a thiolase promoter sequence.

12. A method for producing butanol, comprising the steps of culturing a recombinant microorganism of claim 1 in a culture medium containing glucose, and collecting butanol from a culture thereof.

13. A method for producing butanol, comprising the steps of culturing a recombinant microorganism of claim 8 in a culture medium containing glucose, and collecting butanol from a culture thereof.

14. A vector containing the DNA sequences of SEQ. ID No: 9 and SEQ. ID No: 10.

15. A method of metabolically engineering the recombinant microorganism of claim 1 capable of producing butanol from a substrate, comprising the steps of:

obtaining a microbial host capable of naturally producing butyric acid, and transferring a foreign gene that encodes an enzyme having both alcohol/aldehyde dehydrogenase and butanol hydrogenase activity into the microbial host.

16. The method of claim 15, further comprising the step of transferring to the microbial host a foreign gene for inactivating acetate kinase.

17. The method of claim 15, further comprising the step of transferring to the microbial host a foreign gene for inactivating phosphotransbutyrylase.

18. The method of claim 15, further comprising the step of transferring to the microbial host a foreign gene for inactivating phosphotransacetylase.

19. The method of claim 15, wherein the microbial host is *C. tyrobutyricum.*

20. The method of claim 15, wherein the microbial host is selected from the group consisting of *Clostridium butyricum, Clostridium thermobutyricum, Clostridium cellulovorans, Clostridium carboxidivorans, Butyribacterium methylotrophicum, Clostridium polysaccharolyticum, Clostridium populeti*, and *Clostridium kluyveri.*

21. An isolated and biologically pure culture of a bacterial mutant strain having the ATCC deposit No. PTA-12145.

22. The recombinant microorganism of claim 8, where the foreign gene for inactivating acetate kinase is DNA comprising the base sequence of SEQ. ID NO: 11.

23. The recombinant microorganism of claim 10, wherein the foreign gene for inactivating phosphotransacetylase is DNA comprising the base sequence of SEQ. ID NO: 12.

24. The recombinant organism of claim 11, wherein the thiolase promoter sequence is a DNA comprising the base sequence of SEQ. ID NO: 10.

25. The recombinant microorganism of claim 1, wherein the transfer of SEQ ID NO: 9 is accomplished using a vector that includes pCB102 replicon from *Clostridium butyricum.*

26. The recombinant microorganism of claim 1, wherein the transfer of SEQ ID NO: 9 is accomplished using a vector that includes pBP1 replicon from *Clostridium botulinum.*

* * * * *

```
                          SEQUENCE LISTING

<160> NUMBER OF SEQ ID NOS: 12

<210> SEQ ID NO 1
<211> LENGTH: 37
<212> TYPE: DNA
<213> ORGANISM: Clostridium acetobutylicum, ATCC 824

<400> SEQUENCE: 1

atggatcctt ttataaagga gtgtatataa atgaaag                          37


<210> SEQ ID NO 2
<211> LENGTH: 36
<212> TYPE: DNA
<213> ORGANISM: Clostridium acetobutylicum, ATCC 824

<400> SEQUENCE: 2

ttggcgccat aatgaagcaa agactatttt acattc                           36
```

<210> SEQ ID NO 3
<211> LENGTH: 56
<212> TYPE: DNA
<213> ORGANISM: Clostridium acetobutylicum

<400> SEQUENCE: 3
atggatccat aaatatttag gaggaatagt catgaaagtt acaaatcaaa aagaac 56

<210> SEQ ID NO 4
<211> LENGTH: 38
<212> TYPE: DNA
<213> ORGANISM: Clostridium acetobutylicum

<400> SEQUENCE: 4
tctaccgcgg ataatgaagc aaagactatt ttacattc 38

<210> SEQ ID NO 5
<211> LENGTH: 31
<212> TYPE: DNA
<213> ORGANISM: Clostridium tyrobutyricum

<400> SEQUENCE: 5
agctaagctt ctgaatattc agcgaaaata g 31

<210> SEQ ID NO 6
<211> LENGTH: 51
<212> TYPE: DNA
<213> ORGANISM: Clostridium tyrobutyricum

<400> SEQUENCE: 6
tctaccgcgg acgtcggatc caaatttaaa ttgattacaa acctttttac c 51

<210> SEQ ID NO 7
<211> LENGTH: 7000
<212> TYPE: DNA
<213> ORGANISM: Clostridium acetobutylicum

<400> SEQUENCE: 7
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcg 240
ccattcgcca ttcaggctgc gcaactgttg ggaagggcga tcggtgcggg cctcttcgct 300
attacgccag ctggcgaaag ggggatgtgc tgcaaggcga ttaagttggg taacgccagg 360
gttttcccag tcacgacgtt gtaaaacgac ggccagtgcc aagcttgagc ttaatcgcat 420
ttcatagatt gacctcccaa taactacgtg gtgttattgg gaggtcaatc tatttcattt 480
gcctcttgct caaagttccc aaattcgagt aagaggtatt tttgtttttg gtcgtcgcct 540
ctcattagta gttcagggtt taacattaat actccagttt ttctttttat aatatttcct 600
tcttctaaga ttttaagtgt tgttattact gtttgtagac ttgttcctgt agcttttgct 660
atttctcttg ttgtagctat cattgtattg ttacttaagt ggacattatc taggatatag 720
ttaacgattt taagtttttt tccgccaatc atatctaaca tacttattaa ttgcactata 780
tatgccttta cgaagttacc agacgtttgt ttacggtata acttgtctac ctctatgact 840
tctccacttt cttcgtctat gagcctctga gagcctttat agactgttcc atatctttct 900

-continued

```
ttcatctttt tctcactcct tattttaaac tattctaact atatcataac tgttctaaaa    960
aaaaaagaac atttgttaaa agaaattaga acaaaatgag tgaaaaatta gaacaaacaa   1020
attccttata aaccttatca tctcaaccta tattaagatt ttacctagtt gaatcttctt   1080
ttctatataa agcgtcggag catatcaggg ggttatctaa cgtaaatgct acccttcggc   1140
tcgctttcgc tcggcattga cgtcagatac tgcacccct gaacccccat gctccaacag    1200
caaaaaggaa acttttttgct gcttttccga cgcttattcg cttcgctcat atttatatag   1260
aaaagaagtg aatgcgcaaa agacataatc gattcacaaa aaataggtac acgaaaaaca   1320
agttaaggga tgcagtttat gcatccctta acttacttat taaataattt atagctattg   1380
aaaagagata agaattgttc aaagctaata ttgtttaaat cgtcaattcc tgcatgtttt   1440
aaggaattgt taaattgatt ttttgtaaat attttcttgt attctttgtt aacccatttc   1500
ataacgaaat aattatactt ctgtttatct ttgtgtgata ttcttgattt ttttctattt   1560
aatctgataa gtgagctatt cactttaggt ttaggatgaa aatattctct tggaaccata   1620
cttaatatag aaatatcaac ttctgccatt aaaaataatg ccaatgagcg ttttgtattt   1680
aataatcttt tagcaaaccc gtattccacg attaaataaa tctcatcagc tatactatca   1740
aaaacaattt tgcgtattat atccgtactt atgttataag gtatattacc aaatatttta   1800
taggattggt ttttaggaaa tttaaactgc aatatatcct tgtttaaaac ttggaaatta   1860
tcgtgatcaa caagtttatt ttctgtagtt ttgcataatt tatggtctat ttcaatggca   1920
gttacgaaat tacacctctg tactaattca agggtaaaat gcccttttcc tgagccgatt   1980
tcaaagatat tatcatgttc atttaatctt atatttgtca ttattttatc tatattatgt   2040
tttgaagtaa taaagttttg actgtgtttt atatttttct cgttcattat aaccctcttt   2100
attttttcct ccttataaaa ttagtataat tatagcacga gctctgataa atatgaacat   2160
gatgagtgat cgttaaattt atactgcaat ctgatgcgat tattgaataa aagatatgag   2220
agatttatct agtttctttt tttacaagaa aaaagaaagt tcttaaaggt tttatacttt   2280
tggtcgtaga gcacacggtt taacgactta attacgaagt aaataagtct agtgtgttag   2340
actttaatgt ttttttaagg cattagtgca tttaagcgtc agagcatggc tttatgccga   2400
gaaaactatt ggttggaatg gcgtgtgtgt tagccaaagc tcctgcaggt cgactgtgga   2460
tggagttaag tcagcagaaa gtataatgag aaaatataaa atataaataa ttttctaaaa   2520
aacttaactt catgtgaaaa gtttgttaaa atataaatga gcacgttaat catttaacat   2580
agataattgg atccagaatt taaaaggagg gattaaaatg aactctaaaa taattagatt   2640
tgaaaattta aggtcattct ttaaagatgg gatgacaatt atgattggag gtttttttaaa   2700
ctgtggcact ccaaccaaat taattgattt tttagttaat ttaaatataa agaatttaac   2760
gattataagt aatgatacat gttatcctaa tacaggtatt ggtaagttaa tatcaaataa   2820
tcaagtaaaa aagcttattg cttcatatat aggcagcaac ccagatactg gcaaaaaact   2880
ttttaataat gaacttgaag tagagctctc tccccaagga actctagtgg aaagaatacg   2940
tgcaggcgga tctggcttag gtggtgtact aactaaaaca ggtttaggaa ctttgattga   3000
aaaaggaaag aaaaaaatat ctataaatgg aacggaatat ttgttagagc tacctcttac   3060
agccgatgta gcattaatta aaggtagtat tgtagatgag gccggaaaca ccttctataa   3120
aggtactact aaaaacttta atccctatat ggcaatggca gctaaaaccg taatagttga   3180
agctgaaaat ttagttagct gtgaaaaact agaaaaggaa aaagcaatga cccccggagt   3240
tcttataaat tatatagtaa aggagcctgc ataaaatgat taatgataaa aacctagcga   3300
```

-continued

```
aagaaataat agccaaaaga gttgcaagag aattaaaaaa tggtcaactt gtaaacttag   3360

gtgtaggtct tcctaccatg gttgcagatt atataccaaa aaatttcaaa attactttcc   3420

aatcagaaaa cggaatagtt ggaatgggcg ctagtcctaa aataaatgag gcagataaag   3480

atgtagtaaa tgcaggagga gactatacaa cagtacttcc tgacggcaca tttttcgata   3540

gctcagtttc gttttcacta atccgtggtg gtcacgtaga tgttactgtt ttaggggctc   3600

tccaggtaga tgaaaagggt aatatagcca attggattgt tcctggaaaa atgctctctg   3660

gtatgggtgg agctatggat ttagtaaatg gagctaagaa agtaataatt gcaatgagac   3720

atacaaataa aggtcaacct aaaattttaa aaaaatgtac acttcccctc acggcaaagt   3780

ctcaagcaaa tctaattgta acagaacttg gagtaattga ggttattaat gatggtttac   3840

ttctcactga aattaataaa aacacaacca ttgatgaaat aaggtcttta actgctgcag   3900

atttactcat atccaatgaa cttagaccca tggctgttta gaaagaattc ttgatatcag   3960

gaaggtgact tttatgttaa aggatgaagt aattaaacaa attagcacgc cattaacttc   4020

gcctgcattt cctagaggac cctataaatt tcataatcgt gagtatttta acattgtata   4080

tcgtacagat atggatgctc ttcgtaaagt tgtgccagag cctttagaaa ttgatgagcc   4140

cttagtcagg tttgaaatta tggcaatgca tgatacgagt ggacttggtt gttatacaga   4200

aagcggacag gctattcccg taagctgtaa tggagttaag ggagattatc ttcatatgat   4260

gtatttagat aatgagcctg caattgcagt aggaagggaa ttaagtgcat atcctaaaaa   4320

gctcgggtat ccaaagcttt ttgtggattc agatacttta gtaggaactt tagactatgg   4380

aaaacttaga gttgcgacag ctacaatggg gtacaaacat aaagccttag atgctaatga   4440

agcaaaggat caaatttgtc gccctaatta tatgttgaaa ataataccca attatgatgg   4500

aagccctagg atatgtgagc ttataaatgc gaaaatcaca gatgttaccg tacatgaagc   4560

ttggacagga ccaactcgac tgcagttatt tgatcacgct atggcgccac ttaatgattt   4620

gccagtaaaa gagattgttt ctagctctca cattcttgca gatataatat tgcctagagc   4680

tgaagttata tatgattatc ttaagtaata aaaataagag ttaccttaaa tggtaactct   4740

tattttttta atgtcgactc atagaattcg taatcatggt catagctgtt tcctgtgtga   4800

aattgttatc cgctcacaat tccacacaac atacgagccg gaagcataaa gtgtaaagcc   4860

tggggtgcct aatgagtgag ctaactcaca ttaattgcgt tgcgctcact gcccgctttc   4920

cagtcgggaa acctgtcgtg ccagctgcat taatgaatcg gccaacgcgc ggggagaggc   4980

ggtttgcgta ttgggcgctc ttccgcttcc tcgctcactg actcgctgcg ctcggtcgtt   5040

cggctgcggc gagcggtatc agctcactca aaggcggtaa tacggttatc cacagaatca   5100

ggggataacg caggaaagaa catgtgagca aaaggccagc aaaaggccag gaaccgtaaa   5160

aaggccgcgt tgctggcgtt tttccatagg ctccgccccc ctgacgagca tcacaaaaat   5220

cgacgctcaa gtcagaggtg gcgaaacccg acaggactat aaagatacca ggcgtttccc   5280

cctggaagct ccctcgtgcg ctctcctgtt ccgaccctgc cgcttaccgg atacctgtcc   5340

gcctttctcc cttcgggaag cgtggcgctt tctcaaagct cacgctgtag gtatctcagt   5400

tcggtgtagg tcgttcgctc caagctgggc tgtgtgcacg aaccccccgt tcagcccgac   5460

cgctgcgcct tatccggtaa ctatcgtctt gagtccaacc cggtaagaca cgacttatcg   5520

ccactggcag cagccactgg taacaggatt agcagagcga ggtatgtagg cggtgctaca   5580

gagttcttga agtggtggcc taactacggc tacactagaa gaacagtatt tggtatctgc   5640
```

-continued gctctgctga agccagttac cttcggaaaa agagttggta gctcttgatc cggcaaacaa 5700
accaccgctg gtagcggtgg tttttttgtt tgcaagcagc agattacgcg cagaaaaaaa 5760
ggatctcaag aagatccttt gatcttttct acggggtctg acgctcagtg gaacgaaaac 5820
tcacgttaag ggattttggt catgagatta tcaaaaagga tcttcaccta gatcctttta 5880
aattaaaaat gaagttttaa atcaatctaa agtatatatg agtaaacttg gtctgacagt 5940
taccaatgct taatcagtga ggcacctatc tcagcgatct gtctatttcg ttcatccata 6000
gttgcctgac tccccgtcgt gtagataact acgatacggg agggcttacc atctggcccc 6060
agtgctgcaa tgataccgcg agacccacgc tcaccggctc cagatttatc agcaataaac 6120
cagccagccg gaagggccga gcgcagaagt ggtcctgcaa ctttatccgc ctccatccag 6180
tctattaatt gttgccggga agctagagta agtagttcgc cagttaatag tttgcgcaac 6240
gttgttgcca ttgctacagg catcgtggtg tcacgctcgt cgtttggtat ggcttcattc 6300
agctccggtt cccaacgatc aaggcgagtt acatgatccc ccatgttgtg caaaaaagcg 6360
gttagctcct tcggtcctcc gatcgttgtc agaagtaagt tggccgcagt gttatcactc 6420
atggttatgg cagcactgca taattctctt actgtcatgc catccgtaag atgcttttct 6480
gtgactggtg agtactcaac caagtcattc tgagaatagt gtatgcggcg accgagttgc 6540
tcttgcccgg cgtcaatacg ggataatacc gcgccacata gcagaacttt aaaagtgctc 6600
atcattggaa aacgttcttc ggggcgaaaa ctctcaagga tcttaccgct gttgagatcc 6660
agttcgatgt aacccactcg tgcacccaac tgatcttcag catcttttac tttcaccagc 6720
gtttctgggt gagcaaaaac aggaaggcaa aatgccgcaa aaaagggaat aagggcgaca 6780
cggaaatgtt gaatactcat actcttcctt tttcaatatt attgaagcat ttatcagggt 6840
tattgtctca tgagcggata catatttgaa tgtatttaga aaaataaaca aataggggtt 6900
ccgcgcacat ttccccgaaa agtgccacct gacgtctaag aaaccattat tatcatgaca 6960
ttaacctata aaaataggcg tatcacgagg ccctttcgtc 7000

<210> SEQ ID NO 8
<211> LENGTH: 11845
<212> TYPE: DNA
<213> ORGANISM: Clostridium acetobutylicum

<400> SEQUENCE: 8
agcttataat tatccttacg tgacggttaa gtgcgcccag atagggtgtt aagtcaagta 60
gtttaaggta ctactctgta agataacaca gaaaacagcc aacctaaccg aaaagcgaaa 120
gctgatacgg gaacagagca cggttggaaa gcgatgagtt acctaaagac aatcgggtac 180
gactgagtcg caatgttaat cagatataag gtataagttg tgtttactga acgcaagttt 240
ctaatttcgg tttcacgtcg atagaggaaa gtgtctgaaa cctctagtac aaagaaaggt 300
aagttacgtt aaccgactta tctgttatca ccacatttgt acaatctgta ggagaaccta 360
tgggaacgaa acgaaagcga tgccgagaat ctgaatttac caagacttaa cactaactgg 420 ggataccct a aacaagaatg cctaatagaa aggaggaaaa aggctatagc actagagctt 480
gaaaatcttg caagggtacg gagtactcgt agtagtctga gaagggtaac gccctttaca 540
tggcaaaggg gtacagttat tgtgtactaa aattaaaaat tgattaggga ggaaaacctc 600
aaaatgaaac caacaatggc aattttagaa agaatcagta aaaattcaca agaaaatata 660
gacgaagttt ttacaagact ttatcgttat cttttacgtc cagatattta ttacgtggcg 720
acgcgtgcga ctcatagaat tatttcctcc cgttaaataa tagataacta ttaaaaatag 780

-continued

```
acaatacttg ctcataagta acggtactta aattgtttac tttggcgtgt ttcattgctt    840
gatgaaactg atttttagta aacagttgac gatattctcg attgacccat tttgaaacaa    900
agtacgtata tagcttccaa tatttatctg gaacatctgt ggtatggcgg gtaagtttta    960
ttaagacact gtttactttt ggtttaggat gaaagcattc cgctggcagc ttaagcaatt   1020
gctgaatcga gacttgagtg tgcaagagca accctagtgt tcggtgaata tccaaggtac   1080
gcttgtagaa tccttcttca acaatcagat agatgtcaga cgcatggctt tcaaaaacca   1140
ctttttaat aatttgtgtg cttaaatggt aaggaatact cccaacaatt ttatacctct    1200
gtttgttagg gaattgaaac tgtagaatat cttggtgaat taaagtgaca cgagtattca   1260
gttttaattt ttctgacgat aagttgaata gatgactgtc taattcaata gacgttacct   1320
gtttacttat tttagccagt ttcgtcgtta aatgcccttt acctgttcca atttcgtaaa   1380
cggtatcggt ttcttttaaa ttcaattgtt ttattatttg gttgagtact ttttcactcg   1440
ttaaaaagtt ttgagaatat tttatatttt tgttcatacc agcaccagaa gcaccagcat   1500
ctcttgggtt aattgaggcc tgagtataag gtgacttata cttgtaatct atctaaacgg   1560
ggaacctctc tagtagacaa tcccgtgcta aattgtagga ctgcccttta ataaatactt   1620
ctatatttaa agaggtattt atgaaaagcg gaatttatca gattaaaaat actttctcta   1680
gagaaaattt cgtctggatt agttacttat cgtgtaaaat ctgataaatg gaattggttc   1740
tacataaatg cctaacgact atccctttgg ggagtagggt caagtgactc gaaacgatag   1800
acaacttgct ttaacaagtt ggagatatag tctgctctgc atggtgacat gcagctggat   1860
ataattccgg ggtaagatta acgaccttat ctgaacataa tgccatatga atccctccta   1920
atttatacgt tttctctaac aacttaatta tacccactat tattattttt atcaatataa   1980
cgcgttggga aatggcaatg atagcgaaac aacgtaaaac tcttgttgta tgctttcatt   2040
gtcatcgtca cgtgattcat aaacacaagt gaatgtcgac agtgaatttt tacgaacgaa   2100
caataacaga gccgtatact ccgagagggg tacgtacggt tcccgaagag ggtggtgcaa   2160
accagtcaca gtaatgtgaa caaggcggta cctccctact tcaccatatc attttctgca   2220
gccccctaga aataatttg tttaacttta agaaggagat atacatatat ggctagatcg    2280
tccattccga cagcatcgcc agtcactatg gcgtgctgct agcgctatat gcgttgatgc   2340
aatttctatg cactcgtagt agtctgagaa gggtaacgcc ctttacatgg caaaggggta   2400
cagttattgt gtactaaaat taaaaattga ttagggagga aaacctcaaa atgaaaccaa   2460
caatggcaat tttagaaaga atcagtaaaa attcacaaga aaatatagac gaagttttta   2520
caagacttta tcgttatctt ttacgtccag atatttatta cgtggcgtat caaaatttat   2580
attccaataa aggagcttcc acaaaaggaa tattagatga tacagcggat ggctttagtg   2640
aagaaaaaat aaaaaagatt attcaatctt taaaagacgg aacttactat cctcaacctg   2700
tacgaagaat gtatattgca aaaaagaatt ctaaaaagat gagaccttta ggaattccaa   2760
ctttcacaga taaattgatc caagaagctg tgagaataat tcttgaatct atctatgaac   2820
cggtattcga agatgtgtct cacggtttta gacctcaacg aagctgtcac acagctttga   2880
aaacaatcaa aagagagttt ggcggcgcaa gatggtttgt ggagggagat ataaaaggct   2940
gcttcgataa tatagaccac gttacactca ttggactcat caatcttaaa atcaaagata   3000
tgaaaatgag ccaattgatt tataaatttc taaaagcagg ttatctggaa aactggcagt   3060
atcacaaaac ttacagcgga acacctcaag gtggaattct atctcctctt ttggccaaca   3120
```

-continued

```
tctatcttca tgaattggat aagtttgttt tacaactcaa aatgaagttt gaccgagaaa   3180
gtccagaaag aataacacct gaatatcggg agctccacaa tgagataaaa agaatttctc   3240
accgtctcaa gaagttggag ggtgaagaaa aagctaaagt tcttttagaa tatcaagaaa   3300
aacgtaaaag attacccaca ctcccctgta cctcacagac aaataaagta ttgaaatacg   3360
tccggtatgc ggacgacttc attatctctg ttaaaggaag caaagaggac tgtcaatgga   3420
taaaagaaca attaaaactt tttattcata acaagctaaa aatggaattg agtgaagaaa   3480
aaacactcat cacacatagc agtcaacccg ctcgttttct gggatatgat atacgagtaa   3540
ggagatctgg aacgataaaa cgatctggta aagtcaaaaa gagaacactc aatgggagtg   3600
tagaactcct tattcctctt caagacaaaa ttcgtcaatt tatttttgac aagaaaatag   3660
ctatccaaaa gaaagatagc tcatggtttc cagttcacag gaaatatctt attcgttcaa   3720
cagacttaga aatcatcaca atttataatt ctgaactccg cgggatttgt aattactacg   3780
gtctagcaag taattttaac cagctcaatt attttgctta tcttatggaa tacagctgtc   3840
taaaaacgat agcctccaaa cataagggaa cactttcaaa aaccatttcc atgtttaaag   3900
atggaagtgg ttcgtggggg atcccgtatg agataaagca aggtaagcag cgccgttatt   3960
ttgcaaattt tagtgaatgt aaatcccctt atcaatttac ggatgagata agtcaagctc   4020
ctgtattgta tggctatgcc cggaatactc ttgaaaacag gttaaaagct aaatgttgtg   4080
aattatgtgg gacgtctgat gaaaatactt cctatgaaat tcaccatgtc aataaggtca   4140
aaaatcttaa aggcaaagaa aaatgggaaa tggcaatgat agcgaaacaa cgtaaaactc   4200
ttgttgtatg ctttcattgt catcgtcacg tgattcataa acacaagtga atgtcgagca   4260
cccgttctcg gagcactgtc cgaccgcttt ggccgccgcc cagtcctgct cgcttcgcta   4320
cttggagcca ctatcgacta cgcgatcatg gcgaccacac ccgtcctgtg gatcgccaag   4380
ctcgccgatg gtagtgtggg gtctccccat gcgagagtag ggaactgcca ggcatcaaat   4440
aaaacgaaag gctcagtcga aagactgggc ctttcgtttt atctgttgtt tgtcggtgaa   4500
cgctctcctg agtaggacaa atccgccggg agcggatttg aacgttgcga agcaacggcc   4560
cggagggtgg cgggcaggac gcccgccata aactgccagg catcaaatta agcagaaggc   4620
catcctgacg gatggccttt ttgcgtttct acaaactctt cctgtcgtca tatctacaag   4680
ccatcccccc acagatacgg taaactagcc tcgtttttgc atcaggaaag cagaacgcca   4740
tgagcggcct catttcttat tctgagttac aacagtccgc accgctgtcc ggtagctcct   4800
tccggtgggc gcggggcatg actatcgtcg ccgcacttat gactgtcttc tttatcatgc   4860
aactcgtagg acaggtgcca gcttggcact ggccgtcgtt ttacaacgtc gtgactggga   4920
aaaccctggc gttacccaac ttaatcgcct tgcagcacat ccccctttcg ccagctggcg   4980
taatagcgaa gaggcccgca ccgatcgccc ttcccaacag ttgcgcagcc tgaatggcga   5040
atggcgctag cgaagagatg cagcagccat tatttttttg aacaattgac aattcatttc   5100
ttattttttta ttaagtgata gtcaaaaggc ataacagtgc tgaatagaaa gaaatttaca   5160
gaaaagaaaa ttatagaatt tagtatgatt aattatactc atttatgaat gtttaattga   5220
atacaaaaaa aaatacttgt tatgtattca attacgggtt aaaatataga caagttgaaa   5280
aatttaataa aaaaataagt cctcagctct tatatattaa gctaccaact tagtatataa   5340
gccaaaactt aaatgtgcta ccaacacatc aagccgttag agaactctat ctatagcaat   5400
atttcaaatg taccgacata caagagaaac attaactata tatattcaat ttatgagatt   5460
atcttaacag atataaatgt aaattgcaat aagtaagatt tagaagttta tagcctttgt   5520
```

-continued

```
gtattggaag cagtacgcaa aggctttttt atttgataaa aattagaagt atatttattt   5580
tttcataatt aatttatgaa aatgaaaggg ggtgagcaaa gtgacagagg aaagcagtat   5640
cttatcaaat aacaaggtat tagcaatatc attattgact ttagcagtaa acattatgac   5700
ttttatagtg cttgtagcta agtagtacga aagggggagc tttaaaaagc tccttggaat   5760
acatagaatt cataaattaa tttatgaaaa gaagggcgta tatgaaaact tgtaaaaatt   5820
gcaaagagtt tattaaagat actgaaatat gcaaaataca ttcgttgatg attcatgata   5880
aaacagtagc aacctattgc agtaaataca atgagtcaag atgtttacat aaagggaaag   5940
tccaatgtat taattgttca aagatgaacc gatatggatg gtgtgccata aaaatgagat   6000
gttttacaga ggaagaacag aaaaaagaac gtacatgcat taaatattat gcaaggagct   6060
ttaaaaaagc tcatgtaaag aagagtaaaa agaaaaaata atttatttat taatttaata   6120
ttgagagtgc cgacacagta tgcactaaaa aatatatctg tggtgtagtg agccgataca   6180
aaaggatagt cactcgcatt ttcataatac atcttatgtt atgattatgt gtcggtggga   6240
cttcacgacg aaaacccaca ataaaaaaag agttcggggt agggttaagc atagttgagg   6300
caactaaaca atcaagctag gatatgcagt agcagaccgt aaggtcgttg tttaggtgtg   6360
ttgtaataca tacgctatta agatgtaaaa atacggatac caatgaaggg aaaagtataa   6420
tttttggatg tagtttgttt gttcatctat gggcaaacta cgtccaaagc cgtttccaaa   6480
tctgctaaaa agtatatcct ttctaaaatc aaagtcaagt atgaaatcat aaataaagtt   6540
taattttgaa gttattatga tattatgttt ttctattaaa ataaattaag tatatagaat   6600
agtttaataa tagtatatac ttaatgtgat aagtgtctga cagctgaccg gtctaaagag   6660
gtccctagcg cctacgggga atttgtatcg ataaggggta caaattccca ctaagcgctc   6720
ggcggggatc gatcccgggt acgtacccgg cagtttttct tttcggcaa gtgttcaaga   6780
agttattaag tcgggagtgc agtcgaagtg ggcaagttga aaaattcaca aaaatgtggt   6840
ataatatctt tgttcattag agcgataaac ttgaatttga gagggaactt agatggtatt   6900
tgaaaaaatt gataaaaata gttggaacag aaaagagtat tttgaccact actttgcaag   6960
tgtaccttgt acctacagca tgaccgttaa agtggatatc acacaaataa aggaaaaggg   7020
aatgaaacta tatcctgcaa tgctttatta tattgcaatg attgtaaacc gccattcaga   7080
gtttaggacg gcaatcaatc aagatggtga attggggata tatgatgaga tgataccaag   7140
ctatacaata tttcacaatg atactgaaac attttccagc ctttggactg agtgtaagtc   7200
tgactttaaa tcatttttag cagattatga aagtgatacg caacggtatg gaaacaatca   7260
tagaatggaa ggaaagccaa atgctccgga aaacattttt aatgtatcta tgataccgtg   7320
gtcaaccttc gatggcttta atctgaattt gcagaaagga tatgattatt tgattcctat   7380
ttttactatg ggaaatatt  ataaagaaga taacaaaatt atacttcctt tggcaattca   7440
agttcatcac gcagtatgtg acggatttca catttgccgt tttgtaaacg aattgcagga   7500
attgataaat agttaacttc aggtttgtct gtaactaaaa acaagtattt aagcaaaaac   7560
atcgtagaaa tacggtgttt tttgttaccc taaaatctac aattttatac ataaccacag   7620
gttagtacaa agaccttgtg tttctttttg aaaggcttaa aacaaggatt tttccttgat   7680
ttaagccccg aaaagcaaca caaccaaggt tttagtatca atctgtggtt tttatatttt   7740
cagagaccgg tcaggagtca ggcaactatg gatgaacgaa atagacagat cgctgagata   7800
ggtgcctcac tgattaagca ttggtaactg tcagaccaag tttactcata tatactttag   7860
```

-continued

```
attgatttaa aacttcattt ttaatttaaa aggatctagg tgaagatcct ttttgataat   7920
ctcatgacca aaatccctta acgtgagttt tcgttccact gagcgtcaga ccccgtagaa   7980
aagatcaaag gatcttcttg agatcctttt tttctgcgcg taatctgctg cttgcaaaca   8040
aaaaaaccac cgctaccagc ggtggtttgt ttgccggatc aagagctacc aactcttttt   8100
ccgaaggtaa ctggcttcag cagagcgcag ataccaaata ctgttcttct agtgtagccg   8160
tagttaggcc accacttcaa gaactctgta gcaccgccta catacctcgc tctgctaatc   8220
ctgttaccag tggctgctgc cagtggcgat aagtcgtgtc ttaccgggtt ggactcaaga   8280
cgatagttac cggataaggc gcagcggtcg ggctgaacgg ggggttcgtg cacacagccc   8340
agcttggagc gaacgaccta caccgaactg agatacctac agcgtgagca ttgagaaagc   8400
gccacgcttc ccgaagggag aaaggcggac aggtatccgg taagcggcag ggtcggaaca   8460
ggagagcgca cgagggagct tccaggggga aacgcctggt atctttatag tcctgtcggg   8520
tttcgccacc tctgacttga gcgtcgattt ttgtgatgct cgtcaggggg gcggagccta   8580
tggaaaaacg ccagcaacgc ggccttttta cggttcctgg ccttttgctg gccttttgct   8640
cacatgttct ttcctgcgtt atcccctgat tctgtggata accgtattac cgcctttgag   8700
tgagctgata ccgctcgccg cagccgaacg accgagcgca gcgagtcagt gagcgaggaa   8760
gcggaagcag taagacgggt aagcctgttg atgataccgc tgccttactg ggtgcattag   8820
ccagtctgaa tgacctgtca cgggataatt cctaactcac attaattgcg ttgcgctcac   8880
tgcccgcttt ccagtcggga aacctgtcgt gccagctgca ttaatgaatc ggccaacgcg   8940
cggggagagg cggtttgcgt attgggcgcc agggtggttt ttcttttcac cagtgagacg   9000
ggcaacagct gattgccctt caccgcctgg ccctgagaga gttgcagcaa gcggtccacg   9060
ctggtttgcc ccagcaggcg aaaatcctgt ttgatggtgg ttgacggcgg gatataacat   9120
gagctgtctt cggtatcgtc gtatcccact accgagatat ccgcaccaac gcgcagcccg   9180
gactcggtaa tggcgcgcat tgcgcccagc gccatctgat cgttggcaac cagcatcgca   9240
gtgggaacga tgccctcatt cagcatttgc atggtttgtt gaaaaccgga catggcactc   9300
cagtcgcctt cccgttccgc tatcggctga atttgattgc gagtgagata tttatgccag   9360
ccagccagac gcagacgcgc cgagacagaa cttaatgggc ccgctaacag cgcgatttgc   9420
tggtgaccca atgcgaccag atgctccacg cccagtcgcg taccgtcttc atgggagaaa   9480
ataatactgt tgatgggtgt ctggtcagag acatcaagaa ataacgccgg aacattagtg   9540
caggcagctt ccacagcaat ggcatcctgg tcatccagcg gatagttaat gatcagccca   9600
ctgacgcgtt gcgcgagaag attgtgcacc gccgctttac aggcttcgac gccgcttcgt   9660
tctaccatcg acaccaccac gctggcaccc agttgatcgg cgcgagattt aatcgccgcg   9720
acaatttgcg acggcgcgtg cagggccaga ctggaggtgg caacgccaat cagcaacgac   9780
tgtttgcccg ccagttgttg tgccacgcgg ttgggaatgt aattcagctc cgccatcgcc   9840
gcttccactt tttcccgcgt tttcgcagaa acgtggctgg cctggttcac cacgcgggaa   9900
acggtctgat aagagacacc ggcatactct gcgacatcgt ataacgttac tggtttcata   9960
tgttgcacct ctactttaat aatttttaac ttttatatat gattaattta attgtttgtt  10020
aaatttatat caatcaatgc tatgaatatt tctttatacc ttattgtaac aaaaaaatat  10080
tggaaatgtt gaattttcag aatattattt ttattatatt attaatttta tatattcatt  10140
tttataagat ttcacaacac gaacgtaata taatatatct tcctcatctt ctgaaaagat  10200
tatactaatt ctattcatgt tacttataat cttattttgg taaatcgaat tttcaatta  10260
```

-continued tatgttcggc aacctttatc ccatcaacag ccgctgatat tataccacct gcaaatcctg 10320
ccccttctcc agttggataa agtccgcata catttatact ttcaagtgaa gcatttctat 10380
tcaatctaac tggtgctgat gttcttgtct caattcccgt taaaattgca tcttctcttg 10440
catacccttt tatcttttta tcaaaattta taattccttc tttaagagcc tctacaacat 10500
aatcaggtaa acattctttt aattccctga attatctgca gaattcgccc ttcctgcttc 10560
ggggtcatta tagcgatttt ttcggtatat ccatcctttt tcgcacgata tacaggattt 10620
tgccaaaggg ttcgtgtaga ctttccttgg tgtatccaac ggcgtcagcc gggcaggata 10680
ggtgaagtag gcccacccgc gagcgggtgt tccttcttca ctgtccctta ttcgcacctg 10740
gcggtgctca acgggaatcc tgctctgcga ggctggccgg ctaccgccgg cgtaacagat 10800
gagggcaagc ggatggctga tgaaaccaag ccaaccagga agggcagccc acctatcaag 10860
gtgtactgcc ttccagacga acgaagagcg attgaggaaa aggcggcggc ggccggcatg 10920
agcctgtcgg cctacctgct ggccgtcggc cagggctaca aaatcacggg cgtcgtggac 10980
tatgagcacg tccgcgagct ggcccgcatc aatggcgacc tgggccgcct gggcggcctg 11040
ctgaaactct ggctcaccga cgacccgcgc acggcgcggt tcggtgatgc cacgatcctc 11100
gccctgctgg cgaagatcga agagaagcag gacgagcttg gcaaggtcat gatgggcgtg 11160
gtccgcccga gggcagagcc atgacttttt tagccgctaa aacggccggg gggtgcgcgt 11220
gattgccaag cacgtcccca tgcgctccat caagaagagc gacttcgcgg agctggtgaa 11280
gtacatcacc gacgagcaag gcaagaccga tccccatccc gaagtggtca gactggaaaa 11340
tcagagggca ggaactgcga acagcaaaaa gtcagatagc accacatagc agacccgcca 11400
taaaacgccc tgagagcccg tgacgggctt ttcttgtatt atgggtagtt tccttgcatg 11460
aatccataaa aggcgcccaa tacgcaaacc gcctctcccc gcgcgttggc cgattcatta 11520
atgcagagct tactccccat ccccccagtg aattccccgg atcgagatag tatatgatgc 11580
atattcttta aatatagata aagttataga agcaatagaa gatttaggat ttactgtaat 11640
ataaattaca cttttaaaaa gtttaaaaac atgatacaat aagttatggt tggaattgtt 11700
atccgctcac aattccaact tatgattaaa attttaagga ggtgtatttc atatgaccat 11760
gattacgaat tcgagctcgg tacccgggga tcctctagag tcgacgtcac gcgtccatgg 11820
agatctcgag gcctgcaggc atgca 11845

<210> SEQ ID NO 9
<211> LENGTH: 3015
<212> TYPE: DNA
<213> ORGANISM: Clostridium acetobutylicum ATCC 824

<400> SEQUENCE: 9
attttacttt attctaataa tacgtaatac acccacttat aactagtatt tggcaataaa 60
aatagttata atcattaatt attgttaaat gtttgacaat ctttaattac tgttatataa 120
taatattata gaaaataaaa tgactgcata attttactat agaaatacaa gcgttaaata 180
tgtacatatc aacggtttat cacattagaa gtaaataatg taaggaaacc acactctata 240
atttataagg catcaaagtg tgttatataa tacaataagt tttatttgca atagtttgtt 300
aaatatcaaa ctaataataa attttataaa ggagtgtata taaatgaaag ttacaaatca 360
aaaagaacta aaacaaaagc taaatgaatt gagagaagcg caaaagaagt ttgcaaccta 420
tactcaagag caagttgata aaatttttaa acaatgtgcc atagccgcag ctaaagaaag 480

-continued

```
aataaactta gctaaattag cagtagaaga aacaggaata ggtcttgtag aagataaaat    540
tataaaaaat cattttgcag cagaatatat atacaataaa tataaaaatg aaaaaacttg    600
tggcataata gaccatgacg attctttagg cataacaaag gttgctgaac caattggaat    660
tgttgcagcc atagttccta ctactaatcc aacttccaca gcaattttca aatcattaat    720
ttctttaaaa acaagaaacg caatattctt ttcaccacat ccacgtgcaa aaaaatctac    780
aattgctgca gcaaaattaa ttttagatgc agctgttaaa gcaggagcac ctaaaaatat    840
aataggctgg atagatgagc catcaataga actttctcaa gatttgatga gtgaagctga    900
tataatatta gcaacaggag gtccttcaat ggttaaagcg gcctattcat ctggaaaacc    960
tgcaattggt gttggagcag gaaatacacc agcaataata gatgagagtg cagatataga   1020
tatggcagta agctccataa ttttatcaaa gacttatgac aatggagtaa tatgcgcttc   1080
tgaacaatca atattagtta tgaattcaat atacgaaaaa gttaaagagg aatttgtaaa   1140
acgaggatca tatatactca atcaaaatga aatagctaaa ataaaagaaa ctatgtttaa   1200
aaatggagct attaatgctg acatagttgg aaaatctgct tatataattg ctaaaatggc   1260
aggaattgaa gttcctcaaa ctacaaagat acttataggc gaagtacaat ctgttgaaaa   1320
aagcgagctg ttctcacatg aaaaactatc accagtactt gcaatgtata aagttaagga   1380
ttttgatgaa gctctaaaaa aggcacaaag gctaatagaa ttaggtggaa gtggacacac   1440
gtcatcttta tatatagatt cacaaaacaa taaggataaa gttaaagaat ttggattagc   1500
aatgaaaact tcaaggacat ttattaacat gccttcttca cagggagcaa gcggagattt   1560
atacaatttt gcgatagcac catcatttac tcttggatgc ggcacttggg gaggaaactc   1620
tgtatcgcaa aatgtagagc ctaaacattt attaaatatt aaaagtgttg ctgaaagaag   1680
ggaaaatatg ctttggttta aagtgccaca aaaaatatat tttaaatatg gatgtcttag   1740
atttgcatta aaagaattaa aagatatgaa taagaaaaga gcctttatag taacagataa   1800
agatcttttt aaacttggat atgttaataa aataacaaag gtactagatg agatagatat   1860
taaatacagt atatttacag atattaaatc tgatccaact attgattcag taaaaaaagg   1920
tgctaaagaa atgcttaact ttgaacctga tactataatc tctattggtg gtggatcgcc   1980
aatggatgca gcaaaggtta tgcacttgtt atatgaatat ccagaagcag aaattgaaaa   2040
tctagctata aactttatgg atataagaaa gagaatatgc aatttcccta aattaggtac   2100
aaaggcgatt tcagtagcta ttcctacaac tgctggtacc ggttcagagg caacaccttt   2160
tgcagttata actaatgatg aaacaggaat gaaataccct ttaacttctt atgaattgac   2220
cccaaacatg gcaataatag atactgaatt aatgttaaat atgcctagaa aattaacagc   2280
agcaactgga atagatgcat tagttcatgc tatagaagca tatgtttcgg ttatggctac   2340
ggattatact gatgaattag ccttaagagc aataaaaatg atatttaaat atttgcctag   2400
agcctataaa aatgggacta acgacattga agcaagagaa aaaatggcac atgcctctaa   2460
tattgcgggg atggcatttg caaatgcttt cttaggtgta tgccattcaa tggctcataa   2520
acttggggca atgcatcacg ttccacatgg aattgcttgt gctgtattaa tagaagaagt   2580
tattaaatat aacgctacag actgtccaac aaagcaaaca gcattccctc aatataaatc   2640
tcctaatgct aagagaaaat atgctgaaat tgcagagtat ttgaatttaa agggtactag   2700
cgataccgaa aaggtaacag ccttaataga agctatttca aagttaaaga tagatttgag   2760
tattccacaa aatataagtg ccgctggaat aaataaaaaa gatttttata atacgctaga   2820
taaaatgtca gagcttgctt ttgatgacca atgtacaaca gctaatccta ggtatccact   2880
```

-continued

```
tataagtgaa cttaaggata tctatataaa atcattttaa aaaataaaga atgtaaaata   2940

gtctttgctt cattatatta gcttcatgaa gcacatagac tattttacat tttactcttg   3000

ttttttatct ttcaa                                                    3015
```

<210> SEQ ID NO 10
<211> LENGTH: 1389
<212> TYPE: DNA
<213> ORGANISM: Clostridium tyrobutyricum

<400> SEQUENCE: 10

```
atattcagcg aaaatagtat attatataat tataaattga tgaatagcta gagtggtcag     60

acctcctagc tattgtttta gaaaactttg tgttttttttt aacaaaaata ttgataaatt   120

tttaattatc tagtataatg aagttgttgg taaaaaggtt tgtaatcaat ttaaatttta   180

aaatataaat atttaggagg aatagtcatg agtgaagttg taattgcaag tgccgttaga   240

acagcaatag gtaaatttgg aggtagcttg aagtcagttc cagcaactga tttaggagct   300

ttggttataa aagaagcatt aaaaagagct aatgttaaac cagaacttgt agatgaagtt   360

gtaatgggta atgtattaca ggcaggttta ggtcagaatc cagcaagaca agcattgata   420

aaatcaggta tacctaatac agtccctgga tttactataa ataaagtttg tggttcagga   480

cttagagcag taagtttagc agctcaaatg ataaaagctg gcgatgatga tatcgttgta   540

gctggtggaa tggaaaatat gtctgctgct ccatatgtaa tgcctagtgc aagatgggga   600

caaagaatgt ttgatggtaa gattatagat gaaatggtaa aagacggact ttgggatgct   660

tttaataact atcacatggg tattacggct gaaaatatag cagaaaagtg gaacataaca   720

agacaaatgc aggatgaatt tgcagctgca tcacaacaaa aagcagtagc agctataaaa   780

tctggcaagt ttaaagatga aatagttcca gtagtaatca aggatagaaa aaagggagaa   840

atagtatttg atactgatga attccctaga gatggtgtaa ctgtcgaagg aatatcaaaa   900

ttaaaaccag catttaagaa ggatggtgga actgttacag ctgccaatgc ttcaggtata   960

aatgatgcag ctgcagcatt agttataatg agtgcagaca aagcaaaaga attgggaatt  1020

aaaccacttg ctaaaattac ttcttatgga tcaaaaggct tggatcctag cataatggga  1080

tatggaccat tccatgctac aaaactagca cttaaaaaag ctaatttaac tgtagatgat  1140

ttagatttaa tagaagcaaa cgaagcattt gctgctcaga gtttagctgt tgcaaaagac  1200

ttgaaatttg atatgagcaa agtaaatgta aatggaggag caatagcact tggacatcct  1260

attggagctt caggcgcaag aatacttact actttgcttt atgaaatgca gaaaagagat  1320

tcaaaacgtg gtttagctac attatgtata ggcggtggaa tgggaactgc tataatcgtt  1380

gaaagataa                                                           1389
```

<210> SEQ ID NO 11
<211> LENGTH: 564
<212> TYPE: DNA
<213> ORGANISM: Clostridium tyrobutyricum

<400> SEQUENCE: 11

```
gatacagcat tccaccagac catgcctgca catgcatatc gttatgcttt accaaagttc     60

ctgtatacac aacacaacgt tcgtcgttat ggtttccatg gtaccagtca tgcctatgtt    120

tctgaacgtg gttctgaact cgcggggagc tataaacatg gcggttggtt aacagcacac    180

ttaggcaatg gtagctccac ttgcgccatt tggaatggtc aaagtgtcga tacctccatg    240
```

-continued

```
ggactgactc cgcttgaagg cgtggtcatg ggtactcgta gtggtgatgt tgatccaagt    300

attcatagct tccttgcttc aaatctgggc tgggacatct ataaaattga taaaatgctg    360

aacagtgaat caggcttact gggcttatca gatctttcaa atgatatgcg taccttgatt    420

gaagcttcag aacaaggcaa tgaagatgcg actttggcga ttgaagtatt ctgttatcgt    480

ttagccaaat cacttgcggc attaagttgc ggtttaccgc gtatcgatgg tttattcttt    540

acaggaggta ttggagaaaa ctct                                           564


<210> SEQ ID NO 12
<211> LENGTH: 732
<212> TYPE: DNA
<213> ORGANISM: Clostridium tyrobutyricum

<400> SEQUENCE: 12

gagttgagga aacacaaggg tatgactcct gataaggcga ataagatagt tagagaccca     60

ttgtactttg caacaatgat ggtcaaacta ggagatgctg atggattggt atctggttct    120

atacatacta caggcgatct tttgagacca ggtcttcaaa ttgtaaaaac tgctccagga    180

acttcagtag tttcaagcat atttatgatg gaagttccaa attgtgattt aggtgataat    240

ggtttcttgt tgttttcaga ttgtgctgta aatcctgtac ctaatactga acaattagct    300

gcaatagcta ttagtactgc agaaactgca aaaagtttat gtggtatgga tccaaaagta    360

gctatgcttt cattttcaac taagggaagt gcacaacatg aaaatgtaga taaggtaaga    420

gaagcaacca aacttgctaa acaaatgcaa ccagatctta aaatagacgg agaacttcaa    480

ttggatgctt ctttaataca ggaagttgca aatttaaaag cacctggtag tcctgtagca    540

ggaaaagcaa atgtacttat attccctgaa cttcaagcag gaaatattgg atataaatta    600

gttcaaagat ttgcaaaagc ggaagcaata ggacctatat gtcaaggctt tgcaaaacca    660

ataaatgatt tgtcaagagg atgcagttct gacgatatag taaatgtagt agcaattaca    720

gcagcacagg ct                                                        732
```